(12) United States Patent
Allerton et al.

(10) Patent No.: US 6,794,387 B2
(45) Date of Patent: Sep. 21, 2004

(54) PHARMACEUTICALLY ACTIVE COMPOUNDS

(75) Inventors: Charlotte Moira Norfor Allerton, Sandwich (GB); Kevin Neil Dack, Sandwich (GB); Mark Ian Kemp, Sandwich (GB)

(73) Assignee: Pfizer Inc., New York, NY (US)

( * ) Notice: Subject to any disclaimer, the term of this patent is extended or adjusted under 35 U.S.C. 154(b) by 27 days.

(21) Appl. No.: 10/099,264

(22) Filed: Mar. 14, 2002

(65) Prior Publication Data

US 2002/0177599 A1 Nov. 28, 2002

Related U.S. Application Data

(60) Provisional application No. 60/291,686, filed on May 17, 2001.

(30) Foreign Application Priority Data

Mar. 28, 2001 (GB) .............................................. 0107751

(51) Int. Cl.$^7$ ...................... C07D 487/04; A61K 31/53; A61P 15/00
(52) U.S. Cl. ........................................ 514/243; 544/184
(58) Field of Search ........................... 544/184; 514/243

(56) References Cited

FOREIGN PATENT DOCUMENTS

| EP | 0526004 | 10/1997 |
|---|---|---|
| EP | 1092719 | 4/2001 |
| WO | WO9428902 | 12/1994 |
| WO | WO9967244 | 12/1999 |
| WO | WO0164677 | 9/2001 |

OTHER PUBLICATIONS

Lucas et al. Pharmacological Reviews 52 (3), 375–413, 2000.*

Dumaitre, Bernard, et. al., "Synthesis and Cyclic GMP Phosphodiesterase Inhibitory Activity of a Series of 6–Phenylpyrazolo [3,4–o]pyrimidones," Journal of Medicinal Chemistry, vol. 39, Nr. 8 1996, pp. 1635–1644.

* cited by examiner

Primary Examiner—Richard L. Raymond
Assistant Examiner—Venkataraman Balasubramanian
(74) Attorney, Agent, or Firm—Peter C. Richardson; Gregg C. Benson; Martha G. Munchhof

(57) ABSTRACT

Compounds of general formula (I):

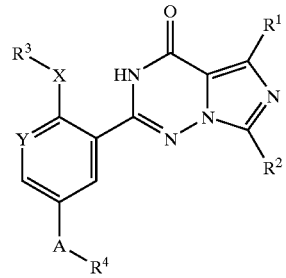

wherein $R^1$, $R^2$, $R^3$, $R^4$, X, Y and A have the meanings given herein which are useful in the curative and prophylactic treatment of a medical condition for which inhibition of a cyclic guanosine 3',5'-monophosphate phosphodiesterase (e.g. cGMP PDE5) is desired.

14 Claims, No Drawings

PHARMACEUTICALLY ACTIVE COMPOUNDS

This application claims priority from U.K. Application 0107751.0 filed Mar. 28, 2001 and U.S. Provisional Application 60/291,686 filed May 17, 2001.

FIELD OF THE INVENTION

This invention relates to pharmaceutically useful compounds, in particular compounds which are useful in the inhibition of cyclic guanosine 3',5'-monophosphate phosphodiesterases (cGMP PDEs), such as type 5 cyclic guanosine 3',5'-monophosphate phosphodiesterases (cGMP PDE5). The compounds therefore have utility in a variety of therapeutic areas, including male erectile dysfunction (MED).

PRIOR ART

Certain cGMP PDE-inhibiting 2-phenyl substituted imidazotriazinone derivatives are disclosed in international patent applications WO 99/24433, WO 99/67244 and WO 01/646777.

DISCLOSURE OF THE INVENTION

According to the present invention, there are provided compounds of general formula I:

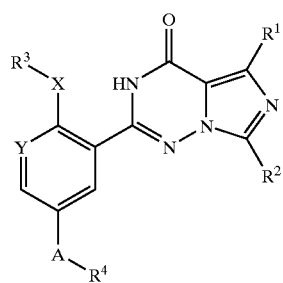

I or pharmaceutically or veterinarily acceptable salts, solvates, polymorphs or pro-drugs thereof wherein:
A represents CHOH or C=O;
X represents O or $NR^5$;
Y represents CH or N;
$R^1$ and $R^2$ independently represent H, $C_1$–$C_6$ alkyl, Het, $C_1$–$C_6$ alkylHet, aryl, $C_1$–$C_6$ alkylaryl, halo, cyano, nitro, $OR^6$, $OC(O)R^6$, $C(O)R^6$, $C(O)OR^6$, $NR^6C(O)NR^7R^8$, $NR^6C(O)OR^6$, $OC(O)NR^7R^8$, $C(O)NR^9R^{10}$, $NR^9R^{10}$, $SO_2NR^9R^{10}$ or $SO_2R^{11}$;
$R^3$, $R^4$ and $R^5$ independently represent H, $C_1$–$C_6$ alkyl, Het, $C_1$–$C_6$ alkylHet, aryl or $C_1$–$C_6$ alkylaryl;
or $R^3$ and $R^5$ together with the nitrogen atom to which they are bound can form a heterocyclic ring which is optionally substituted and/or terminated with one or more substituents selected from: halo, cyano, nitro, $OR^2$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$ or $SO_2R^{17}$;
wherein when $R^1$, $R^2$, $R^3$, $R^4$ or $R^5$ is a $C_1$–$C_6$ alkyl, Het, $C_1$–$C_6$ alkylHet, aryl or $C_1$–$C_6$ alkylaryl group, such $C_1$–$C_6$ alkyl, Het, $C_1$–$C_6$ alkylHet, aryl or $C_1$–$C_6$ alkylaryl group may be optionally substituted and/or terminated with one or more substituents selected from: halo, cyano, nitro, $OR^6$, $OC(O)R^6$, $C(O)R^6$, $C(O)OR^6$, $NR^6C(O)NR^7R^8$, $NR^6C(O)OR^6$, $OC(O)NR^7R^8$, $C(O)NR^9R^{10}$, $NR^9R^{10}$, $SO_2NR^9R^{10}$, $SO_2R^{11}$, $C_1$–$C_6$ alkyl, Het, $C_1$–$C_6$ alkylHet, aryl or $C_1$–$C_6$ alkylaryl;
wherein when $R^1$, $R^2$, $R^3$, $R^4$ or $R^5$ is a $C_1$–$C_6$ alkyl, Het, $C_1$–$C_6$ alkylHet, aryl or $C_1$–$C_6$ alkylaryl group which is substituted and/or terminated with one or more substituents selected from: $C_1$–$C_6$ alkyl, Het, $C_1$–$C_6$ alkylHet, aryl or $C_1$–$C_6$ alkylaryl, such substituent groups are optionally substituted and/or terminated with one or more substituents selected from: halo, cyano, nitro, $OR^{12}$, $OC(O)R^{12}$, $C(O)R^{12}$, $C(O)OR^{12}NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$ or $SO_2R^{17}$;
$R^6$, $R^7$ and $R^8$ independently represent H, $C_1$–$C_6$ alkyl, Het, $C_1$–$C_6$ alkylHet, aryl or $C_1$–$C_6$ alkylaryl;
or $R^7$ and $R^8$ together with the nitrogen atom to which they are bound can form a heterocyclic ring which is optionally substituted and/or terminated with one or more substituents selected from: halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{15}R^{16}$, $C(O)NR^{15}R^{16}$, $NR^{15}R^{16}$, $SO_2NR^{15}R^{16}$ or $SO_2R^{17}$;
$R^9$ and $R^{10}$ independently represent H, $C(O)R^6$, $SO_2R^{11}$, $C_1$–$C_6$ alkyl, Het, $C_1$–$C_6$ alkylHet, aryl or $C_1$–$C_6$ alkylaryl;
or $R^9$ and $R^{10}$ together with the nitrogen atom to which they are bound can form a heterocyclic ring which is optionally substituted and/or terminated with one or more substituents selected from: halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$ or $SO_2R^{17}$;
$R^{11}$ represents $C_1$–$C_6$ alkyl, Het, $C_1$–$C_6$ alkylHet, aryl or $C_1$–$C_6$ alkylaryl;
wherein when $R^6$, $R^7$, $R^8$, $R^9$, $R^{10}$ or $R^{11}$ is a $C_1$–$C_6$ alkyl, Het, $C_1$–$C_6$ or $C_1$–$C_6$ alkylaryl group, such $C_1$–$C_6$ alkyl, Het, $C_1$–$C_6$ alkylHet, aryl or $C_1$–$C_6$ alkylaryl group may be optionally substituted and/or terminated with one or more substituents selected from: halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$ or $SO_2R^{17}$;
$R^{12}$, $R^{13}$ and $R^{14}$ independently represent H or $C_1$–$C_6$ alkyl;
or $R^{13}$ and $R^{14}$ together with the nitrogen atom to which they are bound can form a heterocyclic ring;
$R^{15}$ and $R^{16}$ independently represent H, $C(O)R^{12}$, $SO_2R^{17}$ or $C_1$–$C_6$ alkyl or $R^{15}$ and $R^{16}$ together with the nitrogen atom to which they are bound can form a heterocyclic ring;
$R^{17}$ represents $C_1$–$C_6$ alkyl;
wherein Het represents an optionally substituted four- to twelve-membered heterocyclic group, which group contains one or more heteroatoms selected from nitrogen, oxygen, sulfur and mixtures thereof;
with the proviso that when Y is CH and X is O and A is C(O) then $R^1$, $R^3$ and $R^4$ each do not represent $C_1$–$C_6$ alkyl and R does not represent $C_1$–$C_6$ alkyl or $C_3$–$C_6$ cycloalkyl and
with the further proviso that when Y is CH and X is O and A is CH(OH) then $R^1$ and $R^3$ each do not represent $C_1$–$C_6$ alkyl and R does not represent $C_1$–$C_6$ alkyl or $C_3$–$C_6$ cycloalkyl and $R^4$ is not phenyl or $C_1$–$C_5$ alkyl optionally substituted with up to 2 substituents selected from hydroxy, phenyl, $NR^9R^{10}$ or $OC(O)R^6$ wherein $R^9$ and $R^{10}$ are H, ($C_1$–$C_6$)alkyl, ($C_1$–$C_6$)alkylphenyl or phenyl groups optionally substituted by hydroxy or $OR^{12}$ and $R^6$ is ($C_1$–$C_6$)alkyl optionally substituted by halogen or $OR^{12}$ and wherein $OR^{12}$ is $O(C_1$–$C_6)$alkyl
which compounds are referred to together hereinafter as "the compounds of the invention".

The term "aryl", when used herein, includes six- to ten-membered carbocyclic aromatic groups, such as phenyl and naphthyl.

The term "Het", when used herein, includes four- to twelve-membered, preferably four- to ten-membered, ring systems, which rings contain one or more heteroatoms selected from nitrogen, oxygen, sulfur and mixtures thereof, and which rings may contain one or more double bonds or be non-aromatic, partly aromatic or wholly aromatic in character. The ring systems may be monocyclic, bicyclic or fused. The term thus includes groups such as optionally substituted azetidinyl, pyrrolidinyl, imidazolyl, indolyl, furanyl, oxazolyl, isoxazolyl, oxadiazolyl, thiazolyl, thiadiazolyl, triazolyl, tetrazolyl, oxatriazolyl, thiatriazolyl, pyridazinyl, morpholinyl, pyrimidinyl, pyrazinyl, pyridinyl, quinolinyl, isoquinolinyl, piperidinyl, pyrazolyl, imidazopyridinyl and piperazinyl. Substitution at Het may be at a carbon atom of the Het ring or, where appropriate, at one or more of the heteroatoms.

"Het" groups may also be in the form of an N-oxide.

Preferred Het groups for use herein are $C_5$–$C_8$ membered ring systems containing at least one N and optionally O, S or mixtures thereof. Highly preferred herein for the Het or alkylHet substitutents on $R^1$ and/or $R^2$ are morpholinyl, piperidinyl, pyrazolyl, imidazolyl, triazolyl, pyridinyl or azetidinyl groups.

The heterocyclic ring that $R^3$ and $R^5$, $R^7$ and $R^8$, $R^9$ and $R^{10}$, $R^{13}$ and $R^{14}$ or $R^{15}$ and $R^{16}$ (together with the nitrogen atom to which they are bound) may represent may be any heterocyclic ring that contains at least one nitrogen atom, and which ring forms a stable structure when attached to the remainder of the molecule via the essential nitrogen atom (which, for the avoidance of doubt, is the atom to which $R^3$ and $R^5$, $R^7$ and $R^8$, $R^9$ and $R^{10}$, $R^{13}$ and $R^{14}$ or $R^{15}$ and $R^{16}$ are attached respectively). In this respect, heterocyclic rings that $R^3$ and $R^5$, $R^7$ and $R^8$, $R^9$ and $R^{10}$, $R^{13}$ and $R^{14}$ or $R^{15}$ and $R^{16}$ (together with the nitrogen atom to which they are bound) may represent include four- to twelve-membered, preferably four- to ten-membered, ring systems, which rings contain at least one nitrogen atom and optionally contain one or more further heteroatoms selected from nitrogen, oxygen and/or sulfur, and which rings may contain one or more double bonds or be non-aromatic, partly aromatic or wholly aromatic in character. The term thus includes groups such as azetidinyl, pyrrolidinyl, imidazolyl, indolyl, triazolyl, tetrazolyl, morpholinyl, piperidinyl, pyrazolyl and piperazinyl.

The term "$C_1$–$C_6$ alkyl" (which includes the $C_1$–$C_6$ alkyl part of $C_1$C_6 alkylHet and $C_1$–$C_6$ alkylaryl groups), when used herein, includes methyl, ethyl, propyl, butyl, pentyl and hexyl groups. Unless otherwise specified, alkyl groups may, when there is a sufficient number of carbon atoms, be linear or branched, be saturated or unsaturated or be cyclic, acyclic or part cyclic/acyclic. Preferred $C_1$–$C_6$ alkyl groups for use herein are $C_1$–$C_4$ alkyl groups.

Substituted $C_1$–$C_6$ alkylHet and $C_1$–$C_6$ alkylaryl as defined hereinbefore may have substituents on the ring and/or on the alkyl chain.

Halo groups with which the above-mentioned groups may be substituted or terminated include fluoro, chloro, bromo and iodo.

Compounds of general formula I are referred to herein after as "the compounds of the invention" or "the compounds".

A preferred group of compounds according to a further aspect of the invention, are compounds of formula I as hereinbefore defined, wherein:

A represents CHOH or C=O;
X represents O;
Y represents CH or N;
$R^1$, $R^2$, $R^3$ and $R^4$ independently represent $C_1$–$C_6$ alkyl, Het, $C_1$–$C_6$ alkylHet, aryl or $C_1$–$C_6$ alkylaryl optionally substituted and/or terminated with one or more substituents selected from: halo, $OR^6$, $NR^9R^{10}$, $C_1$–$C_6$ alkyl, Het, $C_1$–$C_6$ alkylHet, aryl or $C_1$–$C_6$ alkylaryl;
wherein when $R^1$, $R^2$, $R^3$ or $R^4$ is a $C_1$–$C_6$ alkyl, Het, $C_1$–$C_6$ alkylHet, aryl or $C_1$–$C_6$ alkylaryl group which is substituted and/or terminated with one or more substituents selected from: $C_1$–$C_6$ alkyl, Het, $C_1$–$C_6$ alkylHet, aryl or $C_1$–$C_6$ alkylaryl, such substituents are optionally substituted and/or terminated with one or more further substituents selected from: halo, $OR^{12}$ or $NR^{15}R^{16}$;
wherein $R^6$, $R^9$, $R^{10}$, $R^{12}$, $R^{15}$ and $R^{16}$ are as hereinbefore defined.
with the proviso that when Y is CH and X is O and A is C(O) then $R^1$, $R^3$ and $R^4$ each do not represent $C_1$–$C_6$ alkyl and $R^2$ does not represent $C_1$–$C_6$ alkyl or $C_3$–$C_6$ cycloalkyl and
with the further proviso that when Y is CH and X is O and A is CH(OH) then $R^1$ and $R^3$ each do not represent $C_1$–$C_6$ alkyl and $R^2$ does not represent $C_1$–$C_6$ alkyl or $C_3$–$C_6$ cycloalkyl and $R^4$ is not phenyl or $C_1$–$C_5$ alkyl optionally substituted with up to 2 substituents selected from hydroxy, phenyl, $NR^9R^{10}$ or $OC(O)R^6$ wherein $R^9$ and $R^{10}$ are H, ($C_1$–$C_6$)alkyl, ($C_1$–$C_6$)alkylphenyl or phenyl groups optionally substituted by hydroxy or $OR^{12}$ and $R^6$ is ($C_1$–$C_6$)alkyl optionally substituted by halogen or $OR^{12}$ and wherein $OR^{12}$ is $O(C_1$–$C_6$)alkyl.

Highly preferred herein are compounds as defined above wherein Y=CH or N, preferably N and A=C(O) and $R^1$=$C_1$–$C_4$ alkyl or $C_1$–$C_4$ alkylHet, preferably $C_1$–$C_3$ alkylHet and $R^2$ and $R^4$ are independently selected from $C_1$–$C_4$ alkyl, preferably $C_1$–$C_3$ alkyl and $R^3$=$C_1$–$C_4$ alkyl, preferably $C_2$—$C_4$ alkyl wherein the Het group is a morpholinyl, piperidinyl, pyrazolyl, imidazolyl, triazolyl, pyridinyl or azetidinyl group, and is preferably morpholinyl or piperidinyl.

According to another aspect of the present invention there are provided preferred compounds of general formula (I) wherein:
A represents CHOH or C=O;
X represents O;
Y represents N;
$R^1$, $R^2$, $R^3$ and $R^4$ independently represent $C_1$–$C_6$ alkyl, Het, $C_1$–$C_6$ alkylHet, aryl or $C_1$–$C_6$ alkylaryl optionally substituted and/or terminated with one or more substituents selected from: halo, $OR^6$, $NR^9R^{10}$, $C_1$–$C_6$ alkyl, Het, $C_1$–$C_6$ alkylHet, aryl or $C_1$–$C_6$ alkylaryl;
wherein when $R^1$, $R^2$, $R^3$ or $R^4$ is a $C_1$–$C_6$ alkyl, Het, $C_1$–$C_6$ alkylHet, aryl or $C_1$–$C_6$ alkylaryl group which is substituted and/or terminated with one or more substituents selected from: $C_1$–$C_6$ alkyl, Het, $C_1$–$C_6$ alkylHet, aryl or $C_1$–$C_6$ alkylaryl, such substituents are optionally substituted and/or terminated with one or more further substituents selected from: halo, $OR^{12}$ or $NR^{15}R^{16}$;
wherein $R^6$, $R^9$, $R^{10}$, $R^{12}$, $R^{15}$ and $R^{16}$ are as hereinbefore defined.

According to a yet further aspect the present invention provides alternative preferred compounds of general formula (I) as defined hereinbefore wherein:
A represents C=O;
X represents O or $NR^5$ and is preferably O;
Y represents CH or N, and is preferably CH;
$R^1$ and $R^2$ independently represent H, Het, $C_1$–$C_6$ alkylHet, aryl, $C_1$–$C_6$ alkylaryl, halo, cyano, nitro, $OR^6$, $OC(O)R^6$, $C(O)R^6$, $C(O)OR^6$, $NR^6C(O)NR^7R^8$, $NR^6C(O)OR^6$, $OC(O)NR^7R^8$, $C(O)NR^9R^{10}$, $NR^9R^{10}$, $SO_2NR^9R^{10}$ or $SO_2R^{11}$;

$R^3$ or $R^4$ independently represent H, Het, $C_1$–$C_6$ alkylHet, aryl or $C_1$–$C_6$ alkylaryl;

$R^5$ independently represents H, $C_1$–$C_6$ alkyl, Het, $C_1$–$C_6$ alkylHet, aryl or $C_1$–$C_6$ alkylaryl;

or $R^3$ and $R^5$ together with the nitrogen atom to which they are bound can form a heterocyclic ring which is optionally substituted and/or terminated with one or more substituents selected from: halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$ or $SO_2R^{17}$;

wherein when $R^1$, $R^2$, R or $R^4$ is a $C_1$–$C_6$ alkyl, Het, $C_1$–$C_6$alkylHet, aryl or $C_1$–$C_6$ alkylaryl group, such Het, $C_1$–$C_6$ alkylHet, aryl or $C_1$–$C_6$ alkylaryl group may be optionally substituted and/or terminated with one or more substituents selected from: halo, cyano, nitro, $OR^6$, $OC(O)R^6$, $C(O)R^6$, $C(O)OR^6$, $NR^6C(O)NR^7R^8$, $NR^6C(O)OR^6$, $OC(O)NR^7R^8$, $C(O)NR^9R^{10}$, $NR^9R^{10}$, $SO_2NR^9R^{10}$, $SO_2R^{11}$, $C_1$–$C_6$ alkyl, Het, $C_1$–$C_6$ alkylHet, aryl or $C_1$–$C_6$ alkylaryl;

wherein when $R^1$, $R^2$, $R^3$ or $R^4$ is a Het, $C_1$–$C_6$ alkylHet, aryl or $C_1$–$C_6$ alkylaryl group which is substituted and/or terminated with one or more substituents selected from: $C_1$–$C_6$ alkyl, Het, $C_1$–$C_6$ alkylHet, aryl or $C_1$–$C_6$ alkylaryl, such substituent groups are optionally substituted and/or terminated with one or more substituents selected from: halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$ or $SO_2R^{17}$;

wherein when $R^5$ independently represents H, $C_1$–$C_6$ alkyl, Het, $C_1$–$C_6$ alkylHet, aryl or $C_1$–$C_6$ alkylaryl group, such $C_1$–$C_6$ alkyl, Het, $C_1$–$C_6$ alkylHet, aryl or $C_1$–$C_6$ alkylaryl group may be optionally substituted and/or terminated with one or more substituents selected from: halo, cyano, nitro, $OR^6$, $OC(O)R^6$, $C(O)R^6$, $C(O)OR^6$, $NR^6C(O)NR^7R^8$, $NR^6C(O)OR^6$, $OC(O)NR^7R^8$, $C(O)NR^9R^{10}$, $NR^9R^{10}$, $SO_2NR^9R^{10}$, $SO_2R^{11}$, $C_1$–$C_6$ alkyl, Het, $C_1$–$C_6$ alkylHet, aryl or $C_1$–$C_6$ alkylaryl;

wherein when $R^5$ is a $C_1$–$C_6$ alkyl, Het, $C_1$–$C_6$ alkylHet, aryl or $C_1$–$C_6$ alkylaryl group which is substituted and/or terminated with one or more substituents selected from: $C_1$–$C_6$ alkyl, Het, $C_1$–$C_6$ alkylHet, aryl or $C_1$–$C_6$ alkylaryl, such substituent groups are optionally substituted and/or terminated with one or more substituents selected from: halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$ or $SO_2R^{17}$;

$R^6$, $R^7$ and $R^8$ independently represent H, $C_1$–$C_6$ alkyl, Het, $C_1$–$C_6$ alkylHet, aryl or $C_1$–$C_6$ alkylaryl;

or $R^7$ and $R^8$ together with the nitrogen atom to which they are bound can form a heterocyclic ring which is optionally substituted and/or terminated with one or more substituents selected from: halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{12}$; $NR^{15}R^{16}$, $SO_2NR^{15}R^{16}$ or $SO_2R^{17}$;

$R^9$ and $R^{10}$ independently represent H, $C(O)R^6$, $SO_2R^{11}$, $C_1$–$C_6$ alkyl, Het, $C_1$–$C_6$ alkylHet, aryl or $C_1$–$C_6$ alkylaryl;

or $R^9$ and $R^{10}$ together with the nitrogen atom to which they are bound can form a heterocyclic ring which is optionally substituted and/or terminated with one or more substituents selected from: halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$ or $SO_2R^{17}$;

$R^{11}$ represents $C_1$–$C_6$ alkyl, Het, $C_1$–$C_6$ alkylHet, aryl or $C_1$–$C_6$ alkylaryl;

wherein when $R^6$, $R^7$, $R^8$, $R^9$, $R^{10}$ or $R^{11}$ is a $C_1$–$C_6$ alkyl, Het, $C_1$–$C_6$ or $C_1$–$C_6$ alkylaryl group, such $C_1$–$C_6$ alkyl, Het, $C_1$–$C_6$ alkylHet, aryl or $C_1$–$C_6$ alkylaryl group may be optionally substituted and/or terminated with one or more substituents selected from: halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$ or $SO_2R^{17}$;

$R^{12}$, $R^{13}$ and $R^{14}$ independently represent H or $C_1$–$C_6$ alkyl; or $R^{13}$ and $R^{14}$ together with the nitrogen atom to which they are bound can form a heterocyclic ring;

$R^{15}$ and $R^{16}$ independently represent H, $C(O)R^{12}$, $SO_2R^{11}$ or $C_1$–$C_6$ alkyl or $R^{15}$ and $R^{16}$ together with the nitrogen atom to which they are bound can form a heterocyclic ring;

$R^{17}$ represents $C_1$–$C_6$ alkyl;

wherein Het represents an optionally substituted four- to twelve-membered heterocyclic group, which group contains one or more heteroatoms selected from nitrogen, oxygen, sulfur and mixtures thereof.

According to an additional aspect the present invention provides alternative preferred compounds of general formula (I) as defined hereinbefore wherein:

A represents CH(OH);

X represents O or $NR^5$ and is preferably O;

Y represents CH or N, and is preferably CH;

$R^1$ and $R^2$ independently represent H, Het, $C_1$–$C_6$ alkylHet, aryl, $C_1$–$C_6$ alkylaryl, halo, cyano, nitro, $OR^6$, $OC(O)R^6$, $C(O)R^6$, $C(O)OR^6$, $NR^6C(O)NR^7R^8$, $NR^6C(O)OR^6$, $OC(O)NR^7R^8$, $C(O)NR^9R^{10}$, $NR^9R^{10}$, $SO_2NR^9R^{10}$ or $SO_2R^{11}$;

$R^3$ represents H, Het, $C_1$–$C_6$ alkylHet, aryl or $C_1$–$C_6$ alkylaryl;

$R^4$ represents H, Het or $C_1$–$C_6$ alkylHet;

$R^5$ independently represents H, $C_1$–$C_6$ alkyl, Het, $C_1$–$C_6$ alkylHet, aryl or $C_1$–$C_6$ alkylaryl;

or $R^3$ and $R^5$ together with the nitrogen atom to which they are bound can form a heterocyclic ring which is optionally substituted and/or terminated with one or more substituents selected from: halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$ or $SO_2R^{17}$;

wherein when $R^1$, $R^2$ or $R^3$ is a $C_1$–$C_6$ alkyl, Het, $C_1$–$C_6$ alkylHet, aryl or $C_1$–$C_6$ alkylaryl group, such Het, $C_1$–$C_6$ alkylHet, aryl or $C_1$–$C_6$ alkylaryl group may be optionally substituted and/or terminated with one or more substituents selected from: halo, cyano, nitro, $OR^6$, $OC(O)R^6$, $C(O)R^6$, $C(O)OR^6$, $NR^6C(O)NR^7R^8$, $NR^6C(O)OR^6$, $OC(O)NR^7R^8$, $C(O)NR^9R^{10}$, $NR^9R^{10}$, $SO_2NR^9R^{10}$, $SO_2R^{11}$, $C_1$–$C_6$ alkyl, Het, $C_1$–$C_6$ alkylHet, aryl or $C_1$–$C_6$ alkylaryl;

wherein when $R^1$, $R^2$ or $R^3$ is a Het, $C_1$–$C_6$ alkylHet, aryl or $C_1$–$C_6$ alkylaryl group which is substituted and/or terminated with one or more substituents selected from: $C_1$–$C_6$ alkyl, Het, $C_1$–$C_6$ alkylHet, aryl or $C_1$–$C_6$ alkylaryl, such substituent groups are optionally substituted and/or terminated with one or more substituents selected from: halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$ or $SO_2R^{17}$;

wherein when $R^4$ is a Het or $C_1-C_6$ alkylHet group, such Het or $C_1-C_6$ alkylHet group may be optionally substituted and/or terminated with one or more substituents selected from: halo, cyano, nitro, $OR^6$, $OC(O)R^6$, $C(O)R^6$, $C(O)OR^6$, $NR^6C(O)NR^7R^8$, $NR^6C(O)OR^6$, $OC(O)NR^7R^8$, $C(O)NR^9R^{10}$, $NR^9R^{10}$, $SO_2NR^9R^{10}$, $SO_2R^{11}$, $C_1-C_6$ alkyl, Het, $C_1-C_6$ alkylHet, aryl or $C_1-C_6$ alkylaryl;

wherein when $R^4$ is a Het or $C_1-C_6$ alkylHet group which is substituted and/or terminated with one or more substituents selected from: $C_1-C_6$ alkyl, Het, $C_1-C_6$ alkylHet, aryl or $C_1-C_6$ alkylaryl, such substituent groups are optionally substituted and/or terminated with one or more substituents selected from: halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$ or $SO_2R^{17}$;

wherein when $R^5$ independently represents H, $C_1-C_6$ alkyl, Het, $C_1-C_6$ alkylHet, aryl or $C_1-C_6$ alkylaryl group, such $C_1-C_6$ alkyl, Het, $C_1-C_6$ alkylHet, aryl or $C_1-C_6$ alkylaryl group may be optionally substituted and/or terminated with one or more substituents selected from: halo, cyano, nitro, $OR^6$, $OC(O)R^6$, $C(O)R^6$, $C(O)OR^6$, $NR^6C(O)NR^7R^8$, $NR^6C(O)OR^6$, $OC(O)NR^7R^8$, $C(O)NR^9R^{10}$, $NR^9R^{10}$, $SO_2NR^9R^{10}$, $SO_2R^{11}$, $C_1-C_6$ alkyl, Het, $C_1-C_6$ alkylHet, aryl or $C_1-C_6$ alkylaryl;

wherein when $R^5$ is a $C_1-C_6$ alkyl, Het, $C_1-C_6$ alkylHet, aryl or $C_1-C_6$ alkylaryl group which is substituted and/or terminated with one or more substituents selected from: $C_1-C_6$ alkyl, Het, $C_1-C_6$ alkylHet, aryl or $C_1-C_6$ alkylaryl, such substituent groups are optionally substituted and/or terminated with one or more substituents selected from: halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$ or $SO_2R^{17}$;

$R^6$, $R^7$ and $R^8$ independently represent H, $C_1-C_6$ alkyl, Het, $C_1-C_6$ alkylHet, aryl or $C_1-C_6$ alkylaryl;

or $R^7$ and $R^8$ together with the nitrogen atom to which they are bound can form a heterocyclic ring which is optionally substituted and/or terminated with one or more substituents selected from: halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$ or $SO_2R^{17}$;

$R^9$ and $R^{10}$ independently represent H, $C(O)R^{12}$, $SO_2R^{11}$, $C_1-C_6$ alkyl, Het, $C_1-C_6$ alkylHet, aryl or $C_1-C_6$ alkylaryl;

or $R^9$ and $R^{10}$ together with the nitrogen atom to which they are bound can form a heterocyclic ring which is optionally substituted and/or terminated with one or more substituents selected from: halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$ or $SO_2R^{17}$;

$R^{11}$ represents $C_1-C_6$ alkyl, Het, $C_1-C_6$ alkylHet, aryl or $C_1-C_6$ alkylaryl;

wherein when $R^6$, $R^7$, $R^8$, $R^9$, $R^{10}$ or $R^{11}$ is a $C_1-C_6$ alkyl, Het, $C_1-C_6$ or $C_1-C_6$ alkylaryl group, such $C_1-C_6$ alkyl, Het, $C_1-C_6$ alkylHet, aryl or $C_1-C_6$ alkylaryl group may be optionally substituted and/or terminated with one or more substituents selected from: halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$ or $SO_2R^{17}$, $R^{12}$, $R^{13}$ and $R^{14}$ independently represent H or $C_1-C_6$ alkyl; or $R^{13}$ and $R^{14}$ together with the nitrogen atom to which they are bound can form a heterocyclic ring;

$R^{15}$ and $R^{16}$ independently represent H, $C(O)R^{12}$, $SO_2R^{17}$ or $C_1-C_6$ alkyl; or $R^{15}$ and $R^{16}$ together with the nitrogen atom to which they are bound can form a heterocyclic ring;

$R^{17}$ represents $C_1-C_6$ alkyl;

wherein Het represents an optionally substituted four- to twelve-membered heterocyclic group, which group contains one or more heteroatoms selected from nitrogen, oxygen, sulfur and mixtures thereof.

According to a yet further aspect the present invention provides compounds of general formula (I):

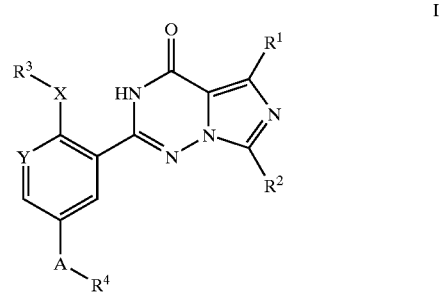

or pharmaceutically or veterinarily acceptable salts, solvates, polymorphs or pro-drugs thereof wherein:

A represents CHOH or C=O;

X represents O or $NR^5$;

Y represents CH or N;

$R^1$ and $R^2$ independently represent H, $C_1-C_6$ alkyl, Het, $C_1-C_6$ alkylHet, aryl, $C_1-C_6$ alkylaryl, halo, cyano, nitro, $OR^6$, $OC(O)R^6$, $C(O)R^6$, $C(O)OR^6$, $NR^6C(O)NR^7R^8$, $NR^6C(O)OR^6$, $OC(O)NR^7R^8$, $C(O)NR^9R^{10}$, $NR^9R^{10}$, $SO_2NR^9R^{10}$ or $SO_2R^{11}$;

$R^3$, $R^4$ and $R^5$ independently represent H, $C_1-C_6$ alkyl, Het, $C_1-C_6$ alkylHet, aryl or $C_1-C_6$ alkylaryl;

or $R^3$ and $R^5$ together with the nitrogen atom to which they are bound can form a heterocyclic ring which is optionally substituted and/or terminated with one or more substituents selected from: halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$;

wherein when $R^1$, $R^2$, $R^3$, $R^4$ or $R^5$ is a $C_1-C_6$ alkyl, Het, $C_1-C_6$ alkylHet, aryl or $C_1-C_6$ alkylaryl group, such $C_1-C_6$ alkyl, Het, $C_1-C_6$ alkylHet, aryl or $C_1-C_6$ alkylaryl group may be optionally substituted and/or terminated with one or more substituents selected from: halo, cyano, nitro, $OR^6$, $OC(O)R^6$, $C(O)R^6$, $C(O)OR^6$, $NR^6C(O)NR^7R^8$, $NR^6C(O)OR^6$, $OC(O)NR^7R^8$, $C(O)NR^9R^{10}$, $NR^9R^{10}$, $SO_2NR^9R^{10}$, $SO_2R^{11}$, $C_1-C_6$ alkyl, Het, $C_1-C_6$ alkylHet, aryl or $C_1-C_6$ alkylaryl;

wherein when $R^1$, $R^2$, $R^3$, $R^4$ or $R^5$ is a $C_1-C_6$ alkyl, Het, $C_1-C_6$ alkylHet, aryl $C_1-C_6$ alkylaryl group which is substituted and/or terminated with one or more substituents selected from: $C_1-C_6$ alkyl, Het, $C_1-C_6$ alkylHet, aryl or $C_1-C_6$ alkylaryl, such substituent groups are optionally substituted and/or terminated with one or more substituents selected from: halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$ or $SO_2R^{17}$;

$R^6$, $R^7$ and $R^8$ independently represent H, $C_1-C_6$ alkyl, Het, $C_1-C_6$ alkylHet, aryl or $C_1-C_6$ alkylaryl;

or $R^7$ and $R^8$ together with the nitrogen atom to which they are bound can form a heterocyclic ring which is optionally substituted and/or terminated with one or more substituents selected from: halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$ or $SO_2R^{17}$;

$R^9$ and $R^{10}$ independently represent H, $C(O)R^6$, $SO_2R^{11}$, $C_1$–$C_6$ alkyl, Het, $C_1$–$C_6$ alkylHet, aryl or $C_1$–$C_6$ alkylaryl;

or $R^9$ and $R^{10}$ together with the nitrogen atom to which they are bound can form a heterocyclic ring which is optionally substituted and/or terminated with one or more substituents selected from: halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$ or $SO_2R^{17}$;

$R^{11}$ represents $C_1$–$C_6$ alkyl, Het, $C_1$–$C_6$ alkylHet, aryl or $C_1$–$C_6$ alkylaryl;

wherein when $R^6$, $R^7$, $R^8$, $R^9$, $R^{10}$ or $R^{11}$ is a $C_1$–$C_6$ alkyl, Het, $C_1$–$C_6$ alkylHet, aryl or $C_1$–$C_6$ alkylaryl group, such $C_1$–$C_6$ alkyl, Het, $C_1$–$C_6$ alkylHet, aryl or $C_1$–$C_6$ alkylaryl group may be optionally substituted and/or terminated with one or more substituents selected from: halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$ or $SO_2R^{17}$;

$R^{12}$, $R^{13}$ and $R^{14}$ independently represent H or $C_1$–$C_6$ alkyl; or $R^{13}$ and $R^{14}$ together with the nitrogen atom to which they are bound can form a heterocyclic ring;

$R^{15}$ and $R^{16}$ independently represent H, $C(O)R^{12}$, $SO_2R^{17}$ or $C_1$–$C_6$ alkyl; or $R^{15}$ and $R^{16}$ together with the nitrogen atom to which they are bound can form a heterocyclic ring;

$R^{17}$ represents $C_1$–$C_6$ alkyl;

Het represents an optionally substituted four- to twelve-membered heterocyclic group, which group contains one or more heteroatoms selected from nitrogen, oxygen, sulfur and mixtures thereof.

The pharmaceutically or veterinarily acceptable salts of the compounds which contain a basic centre are, for example, non-toxic acid addition salts formed with inorganic acids such as hydrochloric, hydrobromic, hydroiodic, sulphuric and phosphoric acid, with carboxylic acids or with organo-sulphonic acids. Examples include the HCl, HBr, HI, sulphate or bisulphate, nitrate, phosphate or hydrogen phosphate, acetate, benzoate, succinate, saccarate, fumarate, maleate, lactate, citrate, tartrate, gluconate, camsylate, methanesulphonate, ethanesulphonate, benzenesulphonate, p-toluenesulphonate and pamoate salts. Compounds of the invention can also provide pharmaceutically or veterinarily acceptable metal salts, in particular non-toxic alkali and alkaline earth metal salts, with bases. Examples include the sodium, potassium, aluminium, calcium, magnesium, zinc and diethanolamine salts. For a review on suitable pharmaceutical salts see Berge et al, J. Pharm, Sci., 66, 1–19, 1977.

The pharmaceutically acceptable solvates of the compounds include the hydrates thereof.

Also included within the scope herein are various salts of the compounds and polymorphs thereof.

Where a compound contains one or more asymmetric carbon atoms and therefore exists in two or more stereoisomeric forms. Where a compound contains an alkenyl or alkenylene group, cis (E) and trans (Z) isomerism may also occur. The present invention includes the individual stereoisomers of the compound and, where appropriate, the individual tautomeric forms thereof, together with mixtures thereof. Separation of diastereoisomers or cis and trans isomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

All stereoisomers of the compounds are included within the scope herein.

The compounds may exhibit tautomerism. All tautomeric forms of the compounds, and mixtures thereof, are included within the scope herein.

Also included within the scope of the application are radiolabelled derivatives of the compounds which are suitable for biological studies.

Preparation

According to a further aspect of the invention there is provided processes for the preparation of compounds of the invention, as illustrated below.

The following processes are illustrative of the general synthetic procedures which may be adopted in order to obtain the compounds of the invention:

1. Compounds of formula I may be prepared by cyclisation of a corresponding compound of formula II:

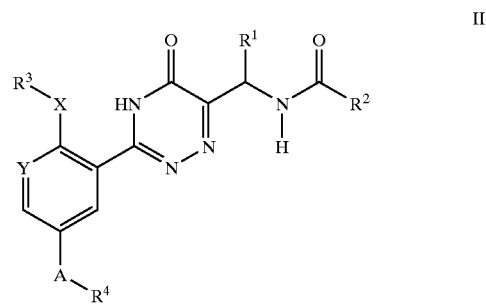

II wherein $R^1$, $R^2$, $R^3$, $R^4$, X, Y and A are as defined previously for compounds of formula I, for example under conditions known to those skilled in the art. Such conditions include reaction, at between room and reflux temperature, in the presence of a suitable (Lewis acidic) dehydrating agent (e.g. phosphorous oxychloride) and an appropriate solvent (e.g. 1,2-dichloroethane), or as otherwise described in the prior art.

Compounds of formula II may be prepared by the reaction of corresponding compounds of formula III:

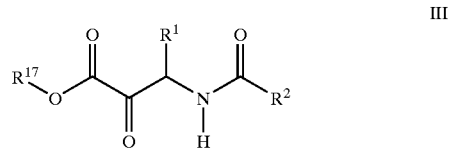

III wherein $R^{17}$ represents $C_1$–$C_6$ alkyl, and $R^1$ and $R^2$ are as defined previously for compounds of formula II, with compounds of formula IV:

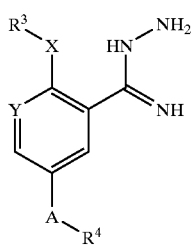

or a suitable acid addition salt thereof (e.g. an hydrogen chloride salt), wherein $R^3$, $R^4$, X, Y and A are as defined previously for compounds of formula II, for example under conditions known to those skilled in the art. Such conditions include, for example, reaction at between room and reflux temperature (e.g. 70° C.) in the presence of a suitable solvent (e.g. ethanol, diethyl ether, 1,4-dioxane or N,N-dimethylformamide).

Compounds of formula III may be prepared via standard techniques, for example by decarboxylation of corresponding compounds of formula V:

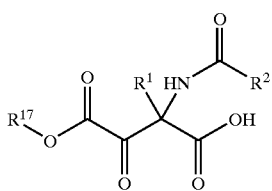

wherein $R^1$, $R^2$ and $R^{17}$ are as defined previously for compounds of formula III, for example under conditions known to those skilled in the art. Such conditions include, for example, reaction at elevated temperature (e.g. reflux temperature) in the presence of a suitable solvent (e.g. methanol or ethanol) and optionally in the presence of a suitable base (e.g. sodium hydrogencarbonate).

Compounds of formula V may be prepared by the reaction of corresponding compounds of formula VI:

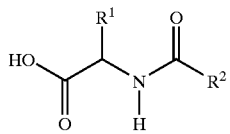

wherein $R^1$ and $R^2$ are as defined previously for compounds of formula V, with compounds of formula VII:

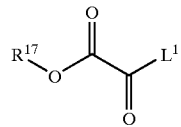

wherein $R^{17}$ is as defined previously for compounds of formula V, and $L^1$ is a leaving group such as halo, preferably chloro, for example under conditions known to those skilled in the art. Such conditions include reaction, at between room and reflux temperature, in the presence of a suitable organic solvent (e.g. THF or ether), an appropriate base (e.g. pyridine, sodium hydride, potassium tert-butoxide, lithium diisopropyl-amide, piperidine or triethylamine) optionally in the presence of a suitable catalyst (e.g. 4-(dimethylamino) pyridine), and optionally with the prior conversion of VI into a 1,3-oxazol-5(4H)-one with excess VII (Dakin-West reaction).

Compounds of formula III may alternatively be prepared by the reaction of corresponding compounds of formula VIII:

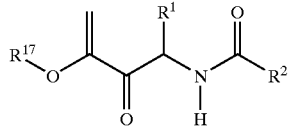

wherein $R^1$, $R^2$ and $R^{17}$ are as defined previously for compounds of formula III, with ozone in a stream of oxygen, followed by reduction of the resulting ozonide, for example, for both steps, under conditions known to those skilled in the art.

Conditions for the ozonation include, for example, reaction at sub-ambient temperature (e.g. −70° C.) in the presence of a suitable solvent (e.g. dichloromethane). Conditions for reduction of the intermediate ozonide include, for example, reaction at sub-ambient temperature (e.g. −70° C.) with a suitable reducing agent (e.g. dimethyl sulfide), followed by treatment (at the same temperature) with an appropriate base (e.g. pyridine).

Compounds of formula VIII may be prepared by the reaction of corresponding compounds of formula IX:

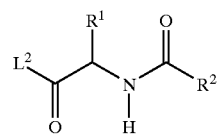

wherein L represents a suitable leaving group (e.g. —N(CH$_3$)OCH$_3$ or chloro) and $R^1$ and $R^2$ are as defined previously for compounds of formula VIII, with a compound of formula X:

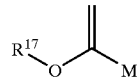

wherein M represents H or a suitable metal-containing moiety (e.g. Na, Li, Mg(II) halide, or a cuprate) and $R^{17}$ is as defined previously for compounds of formula VIII, for example under conditions known to those skilled in the art. Such conditions include, for example, reaction of a compound of formula IX at between −80° C. and room temperature in the presence of a suitable solvent (e.g. THF) with a mixture formed by reacting, at sub-ambient temperature (e.g. −78° C.), a compound of formula X in which M represents H (e.g. ethyl vinyl ether), a suitable organolithium reagent (e.g. tert-butyllithium), an appropriate solvent (e.g. THF) and, optionally, a source of a suitable metal salt (e.g. MgBr$_2$ diethyl etherate).

Compounds of formula IX may be prepared from corresponding compounds of formula VI, as hereinbefore defined, under conditions known to those skilled in the art.

Compounds of formula III may alternatively be prepared by reaction of corresponding compounds of formula XI:

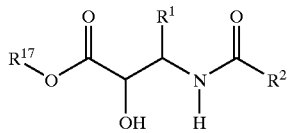

XI wherein $R^1$, $R^2$ and $R^{17}$ are as previously defined for compounds of formula III, with an oxidising agent (e.g. Dess-Martin periodinane) at between −78° C. and reflux temperature in a suitable solvent (e.g. DCM).

Compounds of formula XI may be prepared by the reaction of compounds of formula XII:

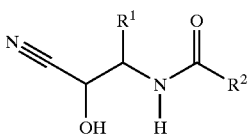

XII wherein $R^1$ and $R^2$ are as previously defined for compounds of formula XI, with $HCl_{(g)}$ in $R^{17}OH$, wherein $R^{17}$ is as previously defined for compounds of formula XI, at between −10° C. and 20° C., followed by reaction with aqueous base (e.g. 10% $Na_2CO_3$ soln.) at between 20° C. and reflux temperature.

Compounds of formula XII may be prepared by the reaction of compounds of formula XIII:

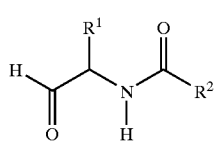

XIII wherein $R^1$ and $R^2$ are as previously defined for compounds of formula XII, with a source of cyamide (e.g. acetone cyanohydrin) in a suitable solvent (e.g. DCM), optionally in the presence of a base (e.g. $Et_3N$), at between 0° C. and reflux temperature.

Compounds of formula XIII may be prepared by the reaction of compounds of formula XIV:

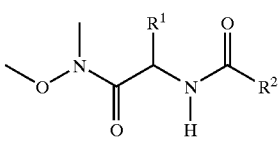

XIV wherein $R^1$ and $R^2$ are as previously defined for compounds of formula XIII, with a source of hydride (e.g. $LiAlH_4$) in a suitable solvent (e.g. THF) at between about −78° C. and 20° C.

Compounds of formula XIV may be prepared from compounds of formula VI using conditions known to those skilled in the art.

Compounds of formula IV may be prepared via standard techniques, for example by reaction of corresponding compounds of formula XV:

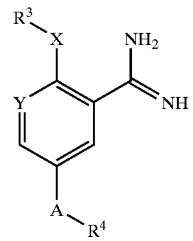

XV or an acid addition salt thereof (e.g. a hydrogen chloride salt), wherein $R^3$, $R^4$, X, Y and A are as defined previously for compounds of formula IV, with hydrazine, for example under conditions known to those skilled in the art. Such conditions include, for example, reaction at between −10° C. and room temperature in the presence of a suitable solvent (e.g. a $C_1$–$C_3$ alcohol), or as otherwise described in the prior art.

In a particular embodiment, a compound of formula IV is formed in situ by reaction at low to ambient temperature (e.g. −10 to 25° C.) of a compound of formula XV with hydrazine hydrate in an alcoholic solution. This is followed by addition of a compound of formula III, after which the mixture is brought to reflux, eventually yielding a compound of formula II.

Compounds of formula XV may be prepared from corresponding compounds of formula XVI, which in turn may be prepared from compounds of formula XVII, which in turn may be prepared from compounds of formula XVIII using conditions known to those skilled in the art:

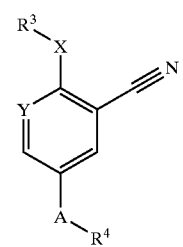

XVI

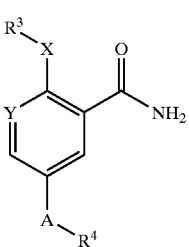

XVII

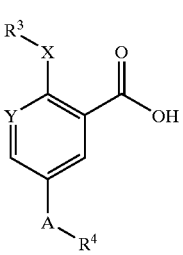

XVIII

Suitable conditions for the amide transformation of the acid XVIII to the corresponding amide compound XVII and for the subsequent dehydration reaction to prepare the nitrile compound XVI from compound XVII and for the ammonia addition or amidine formation reaction from compound XVI to compound XV will be known to the skilled chemist.

Compounds of formula IV may alternatively be prepared by the reaction of compounds of formula XIX:

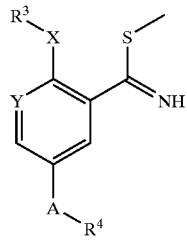

XIX wherein A, Y, X, $R^3$ and $R^4$ are as defined previously for compounds of formula IV, with hydrazine in a suitable solvent (e.g. THF) at between 20° C. and reflux temperature.

Compounds of formula XIX may be prepared by the reaction of compounds of formula XX:

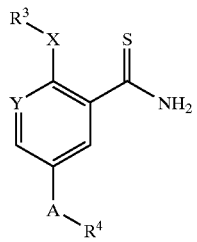

XX wherein A, X, Y, $R^3$ and $R^4$ are as defined previously for compounds of formula XIX, with a methylating agent (e.g. iodomethane) in a suitable solvent (e.g. acetone) at between 20° C. and reflux temperature.

Compounds of formula XX may be prepared by the reaction of compounds of formula XVII with Lawesson's reagent in a suitable solvent (e.g. toluene) at between 20° C. and reflux temperature.

Compounds of formula XVIII, where Y represents CH and A represents C=O, may be prepared from corresponding compounds of formula XXI:

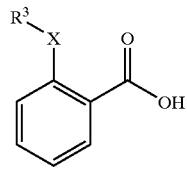

XXI wherein X and $R^3$ are as defined previously for compounds of formula XVIII, by using the Friedel-Crafts acylation reaction. Typical conditions are to use $ClC(O)R^4$, wherein $R^4$ is as defined previously for compounds of formula XVIII, (1 to 3 equivalents) and, optionally, a Lewis acid (e.g. 2 to 10 equivalents $AlCl_3$) in an organic solvent (e.g. dichloromethane) at between 0° C. and reflux temperature.

Alternatively, compounds of formula XVIII, may be prepared from corresponding compounds of formula XXII:

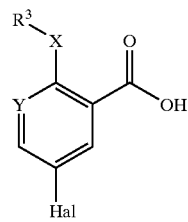

XXII wherein $R^3$, X and Y are as defined previously for compounds of formula XVIII, and Hal represents chloro, bromo or iodo, by conversion of Hal to $AR^4$. This can be achieved by any one of the routes outlined below:

(a) so-called "Heck" conditions (e.g. 2 equivalents of a source of an acyl anion equivalent (such as butyl vinyl ether), 1.7 equivalents of $Et_3N$ and catalytic amounts of $Pd(OAc)_2$ and $P(o-tol)_3$, in MeCN at between room temperature and reflux). Performing a Heck reaction on an alkyl alkenyl ether will give products where A represents C=O. Such reactions are not suitable when $R^4$ is aryl; or (b) so-called "Sonogashira" conditions (for example as described in *Synthesis* 1980, 8, 627, such as 1.5 to 5 equivalents of a terminal alkyne and 0.024 to 0.03 equivalents of $Pd(PPh_3)_2Cl_2/CuI$, in $Et_3N$ and MeCN at between room temperature and 60° C.), followed by hydrolysis of the resultant alkyne (typical conditions 0.3 equivalents $HgSO_4$, $H_2SO_4$, acetone at reflux). Note, this procedure will give products where A represents C=O. Such reactions are not suitable when $R^4$ is aryl; or (c) Halogen/lithium exchange followed by quenching onto an acyl chloride (to give products where A represents C=O). Alternatively, the anion may be quenched onto an aldehyde to give products where A represents CHOH. This alcohol may then be re-oxidised to the corresponding ketone by using standard oxidising agents such as manganese dioxide. Preferred conditions for acyl chloride reaction: 1 to 2 equivalents of n-Butyl Lithium, 1 to 2 equivalents of $R^4COCl$ in THF, at from about −78° C. to about room temperature. If for example $R^4COCl$ is $LCH_2COCl$ (where L is a leaving group such as methanesulphonate, p-toluenesulphonate or halo, preferably chloro or bromo), then once the above procedure has been performed the product can be further functionalised by displacement of L with a nucleophile (e.g. primary or secondary amine); or (d) Formation of Grignard or zincate through addition of magnesium or a zinc source (e.g. zinc, zinc chloride, Reike zinc), followed by quenching onto an acyl chloride (to give products where A represents C=O). Alternatively the Grignard or zinc reagent may be quenched onto an aldehyde to give products where A represents CHOH. Again, the alcohol formed may be oxidised to give the required ketone as detailed hereinbefore; or (e) Carbonylation to yield a carboxylic acid, ester, or Weinreb amide. Preferred conditions: CO (50 psi), $Pd(OAc)_2$ (0.03 equivalents), 1,1'-bis (diphenylphosphino)ferrocene (0.045 equivalents), triethylamine (5 equivalents), and suitable nucleophile (e.g. alcohol, amine) at from 40 to about 80° C. Alternatively the Weinreb amide may be synthesised from the carboxylic acid and the aldehyde may be synthesised from the ester or carboxylic acid. The acid chloride may be formed from the carboxylic acid. Preferred conditions to from acid chloride from acid: (COCl)$_2$ (1.2 equivalents), N,N-dimethylformamide (drop) in dichloromethane. A nucleophile such as a Grignard reagent or zincate may then be reacted with the ester, Weinreb amide or acid chloride to yield products where A represents C=O. Alternatively, analogous reactions with the aldehyde would yield products where A represents CHOH. Preferred conditions for addition of Grignard reagent into acid chloride: RMgBr (1 equivalents), Fe(acac)$_3$ (0.03 equivalents) in THF.

Compounds of formula XXII may be prepared by the halogenation of corresponding compounds of formula XXIII:

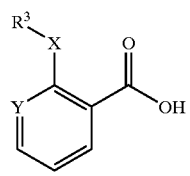

XXIII wherein X, Y and R$^3$ are as defined previously for compounds of formula XXII, via standard techniques. These include iodinating with N-iodosuccinimide (1 to 2 equivalents) in a 4:1 mixture of trifluoroacetic acid and trifluoroacetic anhydride at between room and reflux temperature (suitable when Y represents N). These standard techniques also include brominating with bromine in DCM at temperatures between room temperature and reflux (suitable when Y represents CH).

2. Compounds of formula I may alternatively be prepared from corresponding compounds of formula XXIV:

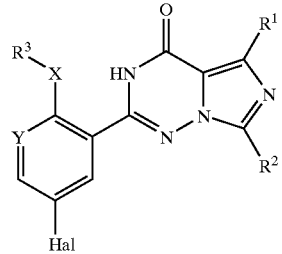

XXIV (f) wherein R$^1$, R$^2$, R$^3$, X and Y are as defined previously for compounds of formula I, and Hal represents chloro, bromo or iodo, by conversion of Hal to AR$^4$. This can be by using conditions described hereinbefore for the synthesis of compounds of formula XVIII from compounds of formula XXII.

Compounds of formula XXIV may be prepared by cyclising corresponding compounds of formula XXV:

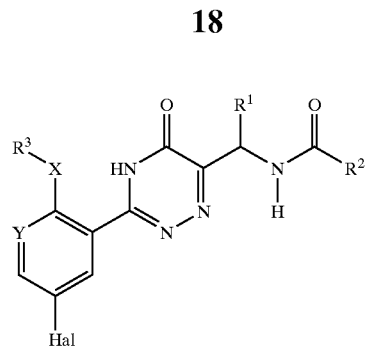

XXV wherein R$^1$, R$^2$, R$^3$, X, Y and Hal are as defined previously for compounds of formula XXIV, using conditions described hereinbefore for the synthesis of compounds of formula I from compounds of formula II.

Compounds of formula XXV may be prepared by the reaction of corresponding compounds of formula XXVI:

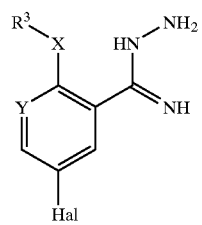

XXVI wherein R$^3$, X, Y and Hal are as defined previously for compounds of formula XXV, with a compound of formula III, for example using the conditions described hereinbefore for the synthesis of compounds of formula II from compounds of formulae III and IV.

Compounds of formula XXVI may be prepared from corresponding compounds of formula XXVII using the procedure described earlier for the preparation of compounds of formula IV from compounds of formula XV.

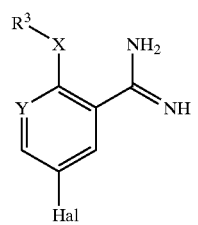

XXVII

Compounds of formula XXVII may be prepared from corresponding compounds of formula XXVIII, which in turn may be prepared from compounds of formula XXIX, which in turn may be prepared from compounds of formula XXII using conditions known to those skilled in the art:

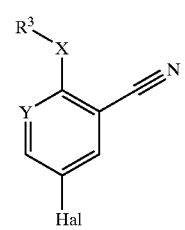

XXVIII

-continued

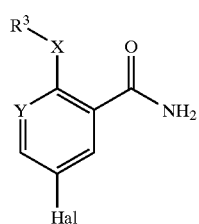
XXIX

Suitable conditions for the amide transformation of compound XXII to compound XXIX and for the dehydration reaction to prepare compound XXVIII from compound XXIX and for the ammonia addition or amidine formation reaction from compound XXVIII to compound XXVII will be known to the skilled chemist.

Compounds of formula XXVI may alternatively be prepared from corresponding compounds of formula XXX:

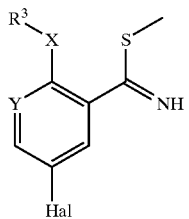
XXX wherein Y, X, Hal and $R^3$ are as defined previously for compounds of formula XXVI, with hydrazine in a suitable solvent (e.g. THF) at between 20° C. and reflux temperature.

Compounds of formula XXX may be prepared by the reaction of compounds of formula XXXI:

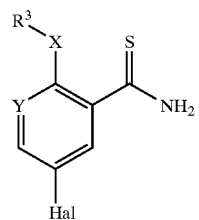
XXXI wherein X, Y, Hal and $R^3$ are as defined previously for compounds of formula XXX, with a methylating agent (e.g. iodomethane) in a suitable solvent (e.g. acetone) at between 20° C. and reflux temperature.

Compounds of formula XXXI may be prepared by the reaction of corresponding compounds of formula XXXII:

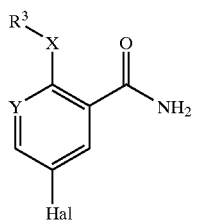
XXXII wherein X, Y, Hal and $R^3$ are as defined previously for compounds of formula XXXI, with Lawesson's reagent in a suitable solvent (e.g. toluene) at between 20° C. and reflux temperature.

Compounds of formula XXXII may be prepared from corresponding compounds of formula XXII by methods known to those skilled in the art.

3. Compounds of formula I may alternatively be prepared from corresponding compounds of formula XXXIII:

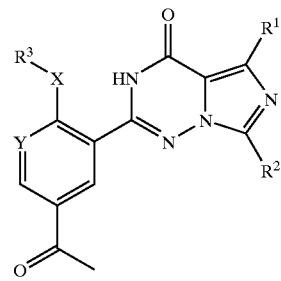
XXXIII wherein $R^1$, $R^2$, $R^3$, X and Y are as defined previously for compounds of formula I, by functionalisation alpha to the methyl ketone. This process is not applicable for compounds of formula I where $R^4$ represents aryl or Het. Examples of functionalisation alpha to the methyl ketone include halogenation, preferably bromination, to form alpha-halo ketones; or oxidation to form alpha-hydroxy ketones. These alpha functionalised ketones may be converted into other compounds of formula I using methods known to those skilled in the art (for example, displacement of the halogen by a suitable nucleophile such as a primary or secondary amine; or conversion of the alcohol to an ether using the Mitsunobu reaction). Preferred conditions for bromination are 1.1 equivalents of N-bromosuccinimide and 3 equivalents of triflic acid in dichloromethane.

Alternatively, addition of a base to compounds of formula XXXIII will form the corresponding enolates, which may then be quenched on to a suitable electrophile (e.g. alkyl halide). Typical conditions for this transformation are 1.1 to 2 equivalents of suitable base (e.g. LDA, NaH) and 1.1 to 2 equivalents of suitable electrophile (e.g. alkyl halides) in THF or ether.

Compounds of formula XXXIII may be prepared by the method described for the preparation of compounds of formula I in process 1.

Alternatively compounds of formula XXXIII may be prepared from corresponding compounds of formula XXIV using conditions hereinbefore defined for the preparation of compounds of formula I from compounds of formula XXIV.

4. Compounds of formula I (where Y represents CH) may alternatively be prepared from corresponding compounds of formula XXXIV:

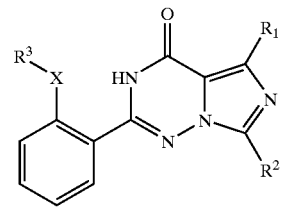
XXXIV wherein $R^1$, $R^2$, $R^3$, and X are as defined previously for compounds of formula I, by using the Friedel-Crafts acylation reaction. Typical conditions are to use an acyl chloride (1 to 3 equivalents) and, optionally, a Lewis acid (e.g. 2 to 10 equivalents $AlCl_3$) in an organic solvent (e.g. dichloromethane) at between 0° C. and reflux temperature.

Compounds of formula XXXIV may be prepared by the cyclisation of corresponding compounds of formula XXXV:

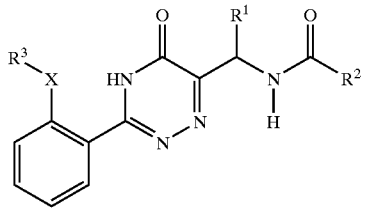

XXXV wherein $R^1$, $R^2$, $R^3$, and X are as defined previously for compounds of formula XXXIV, using conditions described hereinbefore for the synthesis of compounds of formula I from compounds of formula II.

Compounds of formula XXXV may be prepared by the reaction of corresponding compounds of formula XXXVI:

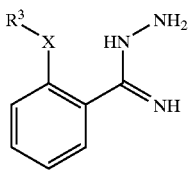

XXXVI wherein $R^3$ and X are as defined previously for compounds of formula XXXV, with a compound of formula III, for example using the conditions described hereinbefore for the synthesis of compounds of formula II from compounds of formulae III and IV.

Compounds of formula XXXVI may be prepared from corresponding compounds of formula XXXVII using the procedure described earlier for the preparation of compounds of formula IV from compounds of formula XV.

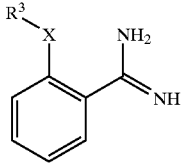

XXXVII

Compounds of formula XXXVII may be prepared from corresponding compounds of formula XXXVIII, which in turn may be prepared from compounds of formula XXXIX, which in turn may be prepared from compounds of formula XXI using conditions known to those skilled in the art:

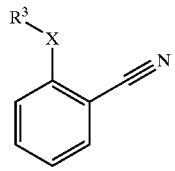

XXXVIII

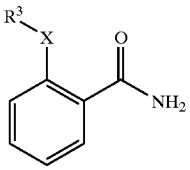

XXXIX

Suitable conditions for the amide transformation of compound XXI to compound XXXIX and for the dehydration reaction to prepare compound XXXVIII from compound XXXIX and for the ammonia addition or amidine formation reaction from compound XXXVIII to compound XXXVII will be known to the skilled chemist.

Compounds of formula XXXVI may alternatively be prepared from corresponding compounds of formula XXXX:

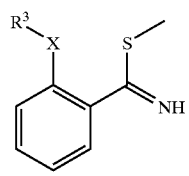

XXXX wherein X and $R^3$ are as defined previously for compounds of formula XXXVI, with hydrazine in a suitable solvent (e.g. THF) at between 20° C. and reflux temperature.

Compounds of formula XXXX may be prepared by the reaction of compounds of formula XXXXI:

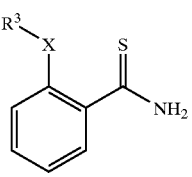

XXXXI wherein X and $R^3$ are as defined previously for compounds of formula XXXX, with a methylating agent (e.g. iodomethane) in a suitable solvent (e.g. acetone) at between 20° C. and reflux temperature.

Compounds of formula XXXXI may be prepared by the reaction of corresponding compounds of formula XXXIX with Lawesson's reagent in a suitable solvent (e.g. toluene) at between 20° C. and reflux temperature. Compounds of formula XXXIX may be prepared from corresponding compounds of formula XXIII by methods known to those skilled in the art.

Compounds of formulae VI, VII, IX, X, XXI, XXIII and derivatives thereof, when not commercially available or not subsequently described, may be obtained either by analogy with the processes described hereinbefore, or by conventional synthetic procedures, in accordance with standard techniques, from readily available starting materials using appropriate reagents and reaction conditions.

When X represents O, $R^3$ can be exchanged for an alternative $R^3$ group ($R^{3a}$) at any step and in any of the processes described hereinbefore by reacting the appropriate intermediate with $R^{3a}OH$ and a base (e.g. cesium carbonate) at reflux temperature (or, if performed in a sealed vessel, at greater than reflux temperature). Likewise, when X represents O, $OR^3$ can be exchanged for $NR^3R^5$ at any step and in any of the processes described hereinbefore by reacting the appropriate intermediate with $HNR^3R^5$, optionally in the presence of catalytic copper sulphate, at temperatures between room and reflux temperature (or, if performed in a sealed vessel, at greater than reflux temperature).

Compounds where A represents CHOH can be prepared at any step and in any of the processes described hereinbefore from corresponding compounds where A represents C=O. This transformation may be achieved by using a suitable reducing agent, preferably sodium borohydride in methanol. Likewise, compounds where A represents C=O can be prepared at any step and in any of the processes described hereinbefore from corresponding compounds where A represents CHOH. This transformation may be achieved by using a suitable oxidising agent (e.g. manganese dioxide).

The compounds of the invention may be isolated from their reaction mixtures using conventional techniques.

It will be appreciated by those skilled in the art that, in the course of carrying out the processes described above, the functional groups of intermediate compounds may need to be protected by protecting groups.

Functional groups which it is desirable to protect include hydroxy, amino and carboxylic acid. Suitable protecting groups for hydroxy include trialkylsilyl and diarylalkylsilyl groups (e.g. tert-butyldimethylsilyl, tert-butyldiphenylsilyl or trimethylsilyl), tetrahydropyranyl and alkylcarbonyl groups (e.g. methyl- and ethylcarbonyl). Suitable protecting groups for amino include tert-butyloxycarbonyl, 9-fluorenylmethoxycarbonyl or benzyloxycarbonyl. Suitable protecting groups for carboxylic acid include $C_{1-6}$ alkyl or benzyl esters.

The protection and deprotection of functional groups may take place before or after any of the reaction steps described hereinbefore.

Protecting groups may be removed in accordance with techniques which are well known to those skilled in the art.

Protection/deprotection strategies as appropriate may be employed such as are known in the literature. Suitable protecting groups for use in accordance with the invention can be found in "Protecting Groups" edited by P. J. Kocienski, Thieme, New York, 1994; and "Protective Groups in Organic Synthesis" $2^{nd}$ edition, T. W. Greeene & P. G. M. Wutz, Wiley-Interscience (1991).

Persons skilled in the art will also appreciate that, in order to obtain compounds of formula I in an alternative, and, on some occasions, more convenient, manner, the individual process steps mentioned hereinbefore may be performed in a different order, and/or the individual reactions may be performed at a different stage in the overall route (i.e. substituents may be added to and/or chemical transformations performed upon, different intermediates to those mentioned hereinbefore in conjunction with a particular reaction). This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis.

Pharmaceutically acceptable acid addition salts of the compounds of formula I that contain a basic centre may be prepared in a conventional manner. For example, a solution of the free base may be treated with the appropriate acid, either neat or in a suitable solvent, and the resulting salt may then be isolated either by filtration or by evaporation under vacuum of the reaction solvent. Pharmaceutically acceptable base addition salts can be obtained in an analogous manner by treating a solution of a compound of formula I with the appropriate base. Both types of salt may be formed or interconverted using ion-exchange resin techniques.

The present invention also includes all suitable isotopic variations of a compound of the formula (I) or a pharmaceutically acceptable salt thereof. An isotopic variation of a compound of the formula (I) or a pharmaceutically acceptable salt thereof is defined as one in which at least one atom is replaced by an atom having the same atomic number but an atomic mass different from the atomic mass usually found in nature. Examples of isotopes that can be incorporated into compounds of the formula (I) and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the compounds of the formula (I) and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the compounds of formula (I) and pharmaceutically acceptable salts thereof of this invention can generally be prepared by conventional procedures such as by the illustrative methods or by the preparations described in the Examples and Preparations hereafter using appropriate isotopic variations of suitable reagents.

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of formula (I) may act as prodrugs of other compounds of formula (I).

All protected derivatives, and prodrugs, of compounds of formula (I) are included within the scope of the invention. Examples of suitable pro-drugs for the compounds of the present invention are described in Drugs of Today, Volume 19, Number 9, 1983, pp 499–538 and in Topics in Chemistry, Chapter 31, pp 306–316 and in "Design of Prodrugs" by H. Bundgaard, Elsevier, 1985, Chapter 1 (the disclosures in which documents are incorporated herein by reference).

It will further be appreciated by those skilled in the art, that certain moieties, known to those skilled in the art as "pro-moieties", for example as described by H. Bundgaard in "design of Prodrugs" (the disclosure in which document is incorporated herein by reference) may be placed on appropriate functionalities when such functionalities are present within compounds of formula (I).

Preferred prodrugs for compounds of formula (I) include: alcohols, esters, carbonate esters, hemi-esters, phosphate esters, nitro esters, sulfate esters, sulphoxides, amides, carbamates, azo-compounds, phosphamides, glycosides, ethers, acetals and ketals.

The present invention additionally comprises the combination of a cGMP $PDE_5$ inhibitor compound as defined herein, wherein said combination can be administered by sequential, simultaneous or joint administration of a compound with:

(1) one or more naturally occurring or synthetic prostaglandins or esters thereof. Suitable prostaglandins for use herein include compounds such as alprostadil, prostaglandin $E_1$, prostaglandin $E_0$, 13, 14-dihydroprostaglandin $E_1$, prostaglandin $E_2$, eprostinol, natural synthetic and semi-synthetic prostaglandins and derivatives thereof including those described in U.S. Pat. No. 6,037,346 issued on Mar. 14, 2000 and incorporated herein by reference, $PGE_0$, $PGE_1$, $PGA_1$, $PGB_1$, $PGF_1$ α, 19-hydroxy $PGA_1$, 19-hydroxy —$PGB_1$, $PGE_2$, $PGB_2$, 19-hydroxy-$PGA_2$, 19-hydroxy-$PGB_2$, $PGE_3α$, carboprost tromethamine dinoprost, tromethamine, dinoprostone, lipo prost, gemeprost, metenoprost, sulprostune, tiaprost and moxisylate; and/or (2) one or more α-adrenergic receptor antagonist compounds also known as α-adrenoceptors or α-receptors or α-blockers. Suitable compounds for use herein include: the α-adrenergic receptors as described in PCT application WO99/30697 published on Jun. 14, 1998, the disclosures of which relating to α-adrenergic receptors are incorporated herein by reference and include, selective $α_1$-adrenoceptors or $α_2$-adrenoceptors and non-selective adrenoceptors, suitable $α_1$-adrenoceptors include: phentolamine, phentolamine mesylate, trazodone, alfuzosin, indoramin, naftopidil, tamsulosin, dapiprazole, phenoxybenzamine, idazoxan, efaraxan, yohimbine, rauwolfa alkaloids, Recordati 15/2739, SNAP 1069, SNAP 5089, RS17053, SL 89.0591, doxazosin, terazosin, abanoquil and prazosin; $α_2$-blockers from U.S. Pat. No. 6,037, 346 [Mar. 14, 2000] dibenamine, tolazoline, trimazosin and dibenamine; α-adrenergic receptors as described in U.S. Pat. Nos. 4,188,390; 4,026,894; 3,511,836; 4,315, 007; 3,527,761; 3,997,666; 2,503,059; 4,703,063; 3,381, 009; 4,252,721 and 2,599,000 each of which is incorporated herein by reference; $α_2$-Adrenoceptors include: clonidine, papaverine, papaverine hydrochloride, optionally in the presence of a cariotonic agent such as pirxamine; and/or (3) one or more NO-donor (NO-agonist) compounds. Suitable NO-donor compounds for use herein include organic nitrates, such as mono- di or tri-nitrates or organic nitrate esters including glyceryl brinitrate (also known as nitroglycerin), isosorbide 5-mononitrate, isosorbide dinitrate, pentaerythritol tetranitrate, erythrityl tetranitrate, sodium nitroprusside (SNP), 3-morpholinosydnonimine molsidomine, S-nitroso-N-acetyl penicilliamine (SNAP) S-nitroso-N-glutathione (SNO-GLU), N-hydroxy-L-arginine, amylnitrate, linsidomine, linsidomine chlorohydrate, (SIN-1) S-nitroso-N-cysteine, diazenium diolates,(NONOates), 1,5-pentanedinitrate, L-arginene, ginseng, zizphi fructus, molsidomine, Re-2047, nitrosylated maxisylyte derivatives such as NMI-678-11 and NMI-937 as described in published PCT application WO 0012075; and/or (4) one or more potassium channel openers. Suitable potassium channel openers for use herein include nicorandil, cromokalim, levcromakalim, lemakalim, pinacidil, cliazoxide, minoxidil, charybdotoxin, glyburide, 4-amini pyridine, $BaCl_2$; and/or (5) one or more dopaminergic agents, preferably apomorphine or a selective D2, D3 or D2/D3 agonist such as pramipexol and ropirinol (as claimed in WO 0023056), L-Dopa or carbi dopa, PNU 95666 (as claimed in WO 0040226); and/or (6) one or more vasodilator agents. Suitable vasodilator agents for use herein include nimodepine, pinacidil, cyclandelate, isoxsuprine, chloroprumazine, halo peridol, Rec 15/2739, trazodone; and/or (7) one or more thromboxane A2 agonists; and/or (8) one or more ergot alkoloids; Suitable ergot alkaloids are described in U.S. Pat. No. 6,037,346 issued on Mar. 14, 2000 and include acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride, terguride; and/or (9) one or more compounds which modulate the action of atrial natruretic factor (also known as atrial naturetic peptide), B and C type naturetic factors such as inhibitors or neutral endopeptidase; and/or

(10) one or more compounds which inhibit angiotensin-converting enzyme such as enapril, and one or more combined inhibitors of angiotensin-converting enzyme and neutral endopeptidase such as omapatrilat; and/or

(11) one or more angiotensin receptor antagonists such as losartan; and/or

(12) one or more substrates for NO-synthase, such as L-arginine; and/or

(13) one or more calcium channel blockers such as amlodipine; and/or

(14) one or more antagonists of endothelin receptors and inhibitors or endothelin-converting enzyme; and/or

(15) one or more cholesterol lowering agents such as statins (e.g. atorvastatin/Lipitor—trade mark) and fibrates; and/or

(16) one or more antiplatelet and antithrombotic agents, e.g. tPA, uPA, warfarin, hirudin and other thrombin inhibitors, heparin, thromboplastin activating factor inhibitors; and/or

(17) one or more insulin sensitising agents such as rezulin and hypoglycaemic agents such as glipizide; and/or

(18) one or more COX 2 inhibitors; and/or

(19) pregabalene; and/or

(20) gabapentene; and/or

(21) one or more acetylcholinesterase inhibitors such as donezipil; and/or

(22) one or more steroidal anti-inflammatory agents; and/or

(23) one or more estrogen agonists and/or estrogen antagonists, preferably raloxifene or lasofoxifene, (−)-cis-6-phenyl-5-[4-(2-pyrrolidin-1-yl-ethoxy)-phenyl]-5,6,7, 8-tetrahydronaphthalene-2-ol and pharmaceutically acceptable salts thereof (compound A below) the preparation of which is detailed in WO 96/21656.

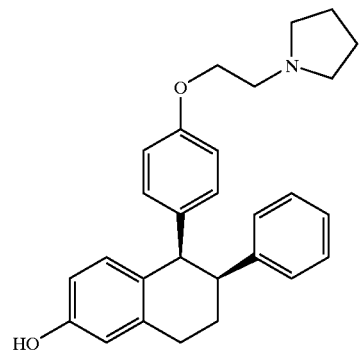

Compound A

(24) one or more one or more of a further PDE inhibitor, more particularly a PDE 2, 4, 7 or 8 inhibitor, preferably PDE2 inhibitor, said inhibitors preferably having an IC50 against the respective enzyme of less than 100 nM: and/or

(25) one or more of an NPY (neuropeptide Y) inhibitor, more particularly NPY1 or NPY5 inhibitor, preferably NPY1 inhibitor, preferably said NPY inhibitors (including NPY Y1 and NPY Y5) having an IC50 of less than 100 nM, more preferably less than 50 nM, suitable NPY and in particular NPY1 inhibitor compounds are described in EP-A-1097718; and/or

(26) one or more of vasoactive intestinal peptide (VIP), VIP mimetic, more particularly mediated by one or more of the VIP receptor subtypes VPAC1, VPAC or PACAP (pituitary adenylate cyclase activating peptide), one or more of a VIP receptor agonist or a VIP analogue (eg Ro-125-1553) or a VIP fragment, one or more of a α-adrenoceptor antagonist with VIP combination (eg Invicorp, Aviptadil); and/or

(27) one or more of a melanocortin receptor agonist or modulator or melanocortin enhancer, such as melanotan 11, PT-14, PT-141 or compounds claimed in WO-09964002, WO-00074679, WO-09955679, WO-00105401, WO-00058361, WO-00114879, WO-00113112, WO-09954358; and/or

(28) one or more of a serotonin receptor agonist, antagonist or modulator, more particularly agonists, antagonists or modulators for 5HT1A (including VML 670), 5HT2A, 5HT2C, 5HT3 and/or 5HT6 receptors, including those described in WO-09902159, WO-00002550 and/or WO-00028993; and/or

(29) one or more of a modulator of transporters for noradrenaline, dopamine and/or serotonin, such as bupropion, GW-320659; and/or

(30) one or more of a purinergic receptor agonist and/or modulator; and/or

(31) one or more of a neurokinin (NK) receptor antagonist, including those described in WO-09964008; and/or

(32) one or more of an opioid receptor agonist, antagonist or modulator, preferably agonists for the ORL-1 receptor; and/or

(33) one or more of an agonist or modulator for oxytocin/vasopressin receptors, preferably a selective oxytocin agonist or modulator; and/or

(34) one or more modulators of cannabinoid receptors; and/or

(35) one or more of an NEP inhibitor, preferably wherein said NEP is EC 3.4.24.11 and more preferably wherein said NEP inhibitor is a selective inhibitor for EC 3.4.24.11, more preferably a selective NEP inhibitor is a selective inhibitor for EC 3.4.24.11, which has an $IC_{50}$ of less than 100 nM (e.g. ompatrilat, sampatrilat) suitable NEP inhibitor compounds are described in EP-A-1097719; and/or

(36) one or more compounds which inhibit angiotensin-converting enzyme such as enalapril, and one or more combined inhibitors of angiotensin-converting enzyme and neutral endopeptidase such as omapatrilat; and/or

(37) one or more tricyclic antidepressants, e.g. amitriptiline; and/or

(38) one or more non-steroidal anti-inflammatory agents; and/or

(39) one or more angiotensin-converting enzyme (ACE) inhibitors, e.g. quinapril; and/or

(40) one or more anti-depressants (such as clomipramine and SSRIs (such as paroxetine and sertaline).

wherein said combination can be in the form of co-administration, simultaneous administration, concurrent administration, or stepwise administration.

Medical Use

The compounds of the invention are useful because they possess pharmacological activity in animals, especially mammals, including humans. They are therefore indicated as pharmaceuticals, as well as for use as animal medicaments.

According to a further aspect of the invention there is provided the compounds of the invention for use as pharmaceuticals, and for use as animal medicaments.

In particular, compounds of the invention have been found to be potent and selective inhibitors of cGMP PDEs, such as cGMP PDE5, for example as demonstrated in the tests described below, and are thus useful in the treatment of medical conditions in humans, and in animals, in which cGMP PDEs, such as cGMP PDE5, are indicated, and in which inhibition of cGMP PDEs, such as cGMP PDE5, is desirable.

By the term "treatment", we include both therapeutic (curative), palliative or prophylactic treatment.

Thus, according to a further aspect of the invention there is provided the use of the compounds of the invention in the manufacture of a medicament for the treatment of a medical condition in which a cGMP PDE (e.g. cGMP PDE5) is indicated. There is further provided the use of the compounds of the invention in the manufacture of a medicament for the treatment of a medical condition in which inhibition of a cGMP PDE (e.g. cGMP PDE5) is desirable.

The compounds of the invention are thus expected to be useful for the curative, palliative or prophylactic treatment of mammalian sexual disorders. In particular, the compounds are of value in the treatment of mammalian sexual dysfunctions such as male erectile dysfunction (MED), impotence, female sexual dysfunction (FSD), (FSD), clitoral dysfunction, female hypoactive sexual desire disorder, female sexual arousal disorder, female sexual pain disorder or female sexual orgasmic dysfunction (FSOD) as well as sexual dysfunction due to spinal cord injury or selective serotonin re-uptake inhibitor (SSRI) induced sexual dysfunction but, clearly, will be useful also for treating other medical conditions for which a potent and selective cGMP PDE5 inhibitor is indicated. Such conditions include premature labour, dysmenorrhoea, benign prostatic hyperplasia (BPH), bladder outlet obstruction, incontinence, stable, unstable and variant (Prinzmetal) angina, hypertension, pulmonary hypertension, chronic obstructive pulmonary disease, coronary artery disease, congestive heart failure, atherosclerosis, conditions of reduced blood vessel patency, e.g. post-percutaneous transluminal coronary angioplasty (post-PTCA), peripheral vascular disease, stroke, nitrate induced tolerance, bronchitis, allergic asthma, chronic asthma, allergic rhinitis, diseases and conditions of the eye such as glaucoma, optic neuropathy, macular degeneration, elevated intra-ocular pressure, retinal or arterial occlusion and diseases characterised by disorders of gut motility, e.g. irritable bowel syndrome (IBS).

Further medical conditions for which a potent and selective cGMP PDE5 inhibitor is indicated, and for which treatment with compounds of the present invention may be useful, include pre-eclampsia, Kawasaki's syndrome, nitrate tolerance, multiple sclerosis, diabetic nephropathy, neuropathy including autonomic and peripheral neuropathy and in particular diabetic neuropathy and symptoms thereof (e.g. gastroparesis), peripheral diabetic neuropathy, Alzheimer's disease, acute respiratory failure, psoriasis, skin necrosis, cancer, metastasis, baldness, nutcracker oesophagus, anal fissure, haemorrhoids, hypoxic vasoconstriction, hypoxic vasoconstriction, diabetes, type 2 diabetes mellitus, the insulin resistance syndrome, insulin resistance, impaired glucose tolerance, as well as the stabilisation of blood pressure during haemodialysis.

Particularly preferred conditions include MED and FSD.

Thus, the invention provides a method of treating or preventing a medical condition for which a cGMP PDE5 inhibitor is indicated, in an animal (e.g. a mammal, including a human being), which comprises administering a therapeutically effective amount of a compound of the invention to a mammal in need of such treatment.

Pharmaceutical Preparations

The compounds will normally be administered orally or by any parenteral route, in the form of pharmaceutical preparations comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

The compounds may also be combined with any other drugs useful in the inhibition of cGMP-PDEs, such as cGMP-PDE5.

The compounds, their pharmaceutically acceptable salts, and pharmaceutically acceptable solvates of either entity can be administered alone but, in human therapy will generally be administered in admixture with a suitable pharmaceutical excipient diluent or carrier selected with regard to the intended route of administration and standard pharmaceutical practice.

For example, the compounds or salts or solvates thereof can be administered orally, buccally or sublingually in the form of tablets, capsules (including soft gel capsules), ovules, elixirs, solutions or suspensions, which may contain flavouring or colouring agents, for immediate-, delayed-, modified-, or controlled-release such as sustained-, dual-, or pulsatile delivery applications. The compounds may also be administered via intracavernosal injection. The compounds may also be administered via fast dispersing or fast dissolving dosages forms.

Such tablets may contain excipients such as microcrystalline cellulose, lactose, sodium citrate, calcium carbonate, dibasic calcium phosphate, glycine and starch (preferably corn, potato or tapioca starch), disintegrants such as sodium starch glycollate, croscarmellose sodium and certain complex silicates, and granulation binders such as polyinylpyrrolidone, hydroxypropylmethyl cellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

Modified release and pulsatile release dosage forms may contain excipients such as those detailed for immediate release dosage forms together with additional excipients that act as release rate modifiers, these being coated on and/or included in the body of the device. Release rate modifiers include, but are not exclusively limited to, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients. Release rate modifying excipients maybe present both within the dosage form i.e. within the matrix, and/or on the dosage form i.e. upon the surface or coating.

Fast dispersing or dissolving dosage formulations (FDDFs) may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol, xylitol. The terms dispersing or dissolving as used herein to describe FDDFs are dependent upon the solubility of the drug substance used i.e. where the drug substance is insoluble a fast dispersing dosage form can be prepared and where the drug substance is soluble a fast dissolving dosage form can be prepared.

The compounds can also be administered parenterally, for example, intracavernosally, intravenously, intra-arterially, intraperitoneally, intrathecally, intraventricularly, intraurethrally intrasternally, intracranially, intramuscularly or subcutaneously, or they may be administered by infusion techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the compounds or salts or solvates thereof will usually be from 10 to 500 mg (in single or divided doses).

Thus, for example, tablets or capsules of the compounds or salts or solvates thereof may contain from 5 mg to 250 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention. The skilled person will also appreciate that, in the treatment of certain conditions (including MED and FSD), compounds may be taken as a single dose on an "as required" basis (i.e. as needed or desired).

Example Tablet Formulation

In general a tablet formulation could typically contain between about 0.01 mg and 500 mg of the compound (or a salt thereof) whilst tablet fill weights may range from 50 mg to 1000 mg. An example formulation for a 10 mg tablet is illustrated:

| Ingredient | % w/w |
|---|---|
| "Active" Compound | 10.000* |
| Lactose | 64.125 |
| Starch | 21.375 |
| Croscarmellose Sodium | 3.000 |
| Magnesium Stearate | 1.500 |

*This quantity is typically adjusted in accordance with drug activity.

Such tablets can be manufactured by standard processes, for example, direct compression or a wet or dry granulation process. The tablet cores may be coated with appropriate overcoats.

The compounds can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark] or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of the compound and a suitable powder base such as lactose or starch.

Aerosol or dry powder formulations are preferably arranged so that each metered dose or "puff" contains from 1 to 50 mg of the compound for delivery to the patient. The overall daily dose with an aerosol will be in the range of from 1 to 50 mg which may be administered in a single dose or, more usually, in divided doses throughout the day.

The compounds may also be formulated for delivery via an atomiser. Formulations for atomiser devices may contain the following ingredients as solubilisers, emulsifiers or suspending agents: water, ethanol, glycerol, propylene glycol, low molecular weight polyethylene glycols, sodium chloride, fluorocarbons, polyethylene glycol ethers, sorbitan trioleate, oleic acid.

Alternatively, the compounds or salts or solvates thereof can be administered in the form of a suppository or pessary, or they may be applied topically in the form of a gel, hydrogel, lotion, solution, cream, ointment or dusting powder. The compounds or salts or solvates thereof may also be dermally administered. The compounds or salts or solvates thereof may also be transdermally administered, for example, by the use of a skin patch. They may also be administered by the ocular, pulmonary or rectal routes.

For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds or salts or solvates thereof can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compounds may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

Generally, in humans, oral administration of the compounds is the preferred route, being the most convenient and, for example in MED, avoiding the well-known disadvantages associated with intracavernosal (i.c.) administration. A preferred oral dosing regimen in MED for a typical man is from 25 to 250 mg of compound when required. In circumstances where the recipient suffers from a swallowing disorder or from impairment of drug absorption after oral administration, the drug may be administered parenterally, sublingually or buccally.

For veterinary use, the compound, or a veterinarily acceptable salt thereof, or a veterinarily acceptable solvate or pro-drug thereof, is administered as a suitably acceptable formulation in accordance with normal veterinary practice and the veterinary surgeon will determine the dosing regimen and route of administration which will be most appropriate for a particular animal.

Thus, according to a further aspect there is provided a pharmaceutical formulation including a compound as detailed hereinbefore in admixture with a pharmaceutically or veterinarily acceptable adjuvant, diluent or carrier.

In addition to the fact that the compounds inhibit cyclic guanosine 3',5'-monophosphate phosphodiesterases (cGMP PDEs) and in particular, are potent and selective inhibitors of cGMP PDE5, the compounds may also have the advantage that they may be more efficacious than, be less toxic than, have a broader range of activity than, be more potent than, produce fewer side effects than, be more easily absorbed than, or they may have other useful pharmacological properties over, compounds known in the prior art.

The biological activities of the compounds were determined by the following test methods.

Phosphodiesterase (PDE) Inhibitory Activity

Compounds of the present invention are potent and selective cGMP PDE5 inhibitors. In vitro PDE inhibitory activities against cyclic guanosine 3',5'-monophosphate (cGMP) and cyclic adenosine 3',5'-monophosphate (cAMP) phosphodiesterases were determined by measurement of their $IC_{50}$ values (the concentration of compound required for 50% inhibition of enzyme activity).

The required PDE enzymes were isolated from a variety of sources, including human corpus cavernosum, human platelets, human cardiac ventricle, human skeletal muscle and human and canine retina, essentially by the method of W. J. Thompson and M. M. Appleman (Biochem., 1971, 10, 311). In particular, the cGMP-specific PDE (PDE5) and the cGMP-inhibited cAMP PDE (PDE3) were obtained from human corpus cavernosum tissue or human platelets; the cGMP-stimulated PDE (PDE2) was obtained from human corpus cavernosum or human platelets; the calcium/calmodulin (Ca/CAM)-dependent PDE (PDE1) from human cardiac ventricle; the cAMP-specific PDE (PDE4) from recombinant clone or human skeletal muscle; and the photoreceptor PDE (PDE6) from canine or human retina. Phosphodiesterases 7–11 were generated from full length human recombinant clones transfected into SF9 cells.

Assays were performed either using a modification of the "batch" method of W. J. Thompson et al. (Biochem., 1979, 18, 5228) or using a scintillation proximity assay for the direct detection of AMP/GMP using a modification of the protocol described by Amersham plc under product code TRKQ7090/7100. In summary, the effect of PDE inhibitors was investigated by assaying a fixed amount of enzyme in the presence of varying inhibitor concentrations and low substrate, (cGMP or cAMP in a 3:1 ratio unlabelled to [$^3$H]-labeled at a conc ~½ $K_m$) such that $IC_{50} \cong Ki$. The final assay volume was made up to 102 μl with assay buffer [20 mM Tris-HCl pH 7.4, 5 mM $MgCl_2$, 1 mg/ml bovine serum albumin]. Reactions were initiated with enzyme, incubated for 30–60 min at 30° C. to give <30% substrate turnover and terminated with 50 μl yttrium silicate SPA beads (containing 3 mM of the respective unlabelled cyclic nucleotide for PDEs 3, 9 and 11). Plates were re-sealed and shaken for 20 min, after which the beads were allowed to settle for 30 min in the dark and then counted on a TopCount plate reader (Packard, Meriden, Conn.). Radioactivity units were converted to % activity of an uninhibited control (100%), plotted against inhibitor concentration and inhibitor $IC_{50}$ values obtained using the 'Fit Curve' Microsoft Excel extension or in-house equivalent. Results from these tests show that the compounds of the present invention are potent and selective inhibitors of cGMP-specific PDE5.

In vitro Metabolism

In vitro metabolism experiments were carried out in the hepatic microsomal fractions from man. Transplant-quality human liver tissue was obtained from the International Institute for the Advancement of Medicine (Exton, Pa., USA). Microsomes were prepared according to the method described in *Biochemical Pharmacology*, 1966, 48, 2147–2156 and stored at −80° C. The concentrations of protein and cytochrome P450 were determined by standard methods described in *Journal of Biological Chemistry*, 1951, 193, 265–275 and *Journal of Biological Chemistry*, 1964, 239, 2370–2378.

Microsomal incubations (1.5 ml) were prepared containing 0.5 μM cytochrome P450, 200 mM phosphate buffer (pH 7.4), 0.1 M $MgCl_2$, 0.1 M isocitric acid, 1 unit/ml isocitrate dehydrogenase and 20 mM β-NADP. Compounds under study were added after a 5 min preincubation at 37° C. to give an initial substrate concentration of 1 μM. The mixture was incubated at 37° C. and samples (100 μl) were removed for analysis for up to 60 min. Metabolism in samples was terminated by the addition of NaOH (0.1 M) containing an internal standard (chosen to have similar physicochemical properties to compounds under study), followed by extraction into ethyl acetate (2 ml). The extracts were evaporated to dryness and analysed by LC-MS/MS (Hewlett Packard HP1100 binary pump, Hypersil HS100 C18, 5 cm by 4.6 mm internal diameter, 5 μm column using a mobile phase of 2 mM ammonium acetate in 90:10 methanol/water, aqueous portion adjusted to pH 4 with glacial acetic acid, and a flowrate of 1 ml/min). The mass spectrometer was a Sciex API 2000 with TurbolonSpray interface using a positive ion multiple reaction monitoring (MRM) detection mode. Nitrogen was used as curtain, nebuliser, TurbolonSpray and collision gases, and the TurbolonSpray temperature was 100° C. Typical voltages were as follows: IS=5.2 kV; RNG=380 V; Q0=−10 V; IQ1=−11 V; ST=−151RO1=−11 V; MU=gain adjusted as per Sciex user manual. Collision energy was 55 eV for high MRM, OR=65 V. Dwell time was 200 msec with a 50 msec pause. Data was acquired using MSExpress v 1.1 and processed using Macquan 1.5 (PE Sciex)). Disappearance rate constants (k) in human microsomal preparations were determined by linear regression of the log ratio (compound under study/internal standard) versus time. The in vitro human microsomal half-lives were determined according to the equation $t_{1/2}$=In 2/k. Results from these studies show that the compounds of the present invention demonstrate desirable human liver microsome (HLM) half-lives.

Those skilled in the art will recognise that an increase in HLM half-life is predictive of reduced clearance in man for compounds cleared predominantly by cytochrome P450 mediated metabolism.

A particular advantage of compounds of the invention, such as for example the compound of Example 1, is desirable in vitro microsomal half-lives. Particularly preferred compounds herein have 2-fold preferably 4-fold and more preferably 5-fold improvements versus compound of the art. Such improved in vitro microsomal half-lives are indicative of reduced clearance in vivo.

Preferred compounds of formula (I) herein have $IC_{50}$ values of less than about 10 nM for the PDE5 enzyme. A more preferred group of compounds have $IC_{50}$ values of less than about 5 nM for the PDE5 enzyme. Highly preferred herein are compounds which have $IC_{50}$ values of less than about 3 nM for the PDE5 enzyme.

In addition, preferred compounds of formula (I) herein have greater than 5-fold selectivity for the PDE5 enzyme versus the PDE6 enzyme. Highly preferred herein are compounds having greater than 10-fold selectivity for the PDE5 enzyme versus the PDE6 enzyme. More preferable herein are compounds having greater than 20-fold selectivity for the PDE5 enzyme versus the PDE6 enzyme and especially preferred are compounds having greater than 30-fold selectivity for the PDE5 enzyme versus the PDE6 enzyme.

Especially preferred herein are compounds which have an $IC_{50}$ value of less than about 10, more preferably less than about 5 nM and especially less than about 3 nM for the PDE5 enzyme in combination with greater than 10-fold, preferably greater than about 20-fold and especially greater than 30-fold selectivity for the PDE5 enzyme versus the PDE6 enzyme.

As detailed hereinbefore preferred compounds herein have desirable human liver microsome (HLM) half-lives. Especially preferred herein are compounds having HLM half-lives of greater than about 20 minutes, more preferably greater than 60 minutes, and most preferably greater than 120 minutes. Such HLM values can be measured according to the methods detailed hereinbefore.

Thus an especially preferred group of compounds herein have an $IC_{50}$ value of less than about 10, more preferably less than about 5 nM and especially less than about 3 nM for the PDE5 enzyme in combination with greater than 10-fold, preferably greater than about 20-fold and especially greater than 30-fold selectivity for the PDE5 enzyme versus the PDE6 enzyme and HLM half-lives of greater than about 20 minutes.

Functional Activity

This can be assessed in vitro by determining the capacity of a compound of the invention to enhance sodium nitroprusside-induced relaxation of pre-contracted rabbit corpus cavernosum tissue strips, as described by S. A. Ballard et al. (Brit. J. Pharmacol., 1996,118 (suppl.), abstract 153P).

In vivo Activity

In vivo activity can be tested by screening test compounds in anaesthetised dogs to determine their capacity, after i.v. administration, to enhance the pressure rises in the corpora cavernosa of the penis induced by intracavernosal injection of sodium nitroprusside, using a method based on that described by Trigo-Rocha et al. (Neurourol. and Urodyn., 1994, 13, 71).

Safety Profile

The compounds may be tested at varying i.v and p.o. doses in animals such as mouse and dog, observing for any untoward effects.

EXAMPLES AND PREPARATIONS

The synthesis of the compounds of general formula (I) and of the intermediates for use therein can be achieved by analogy with the processes of the Examples and Preparations hereinafter.

$^1$H nuclear magnetic resonance (NMR) spectra were recorded using either a Varian Unity 300 or a Varian Inova 400 spectrometer and were in all cases consistent with the proposed structures. Characteristic chemical shifts ($\delta$) are given in parts-per-million downfield from tetramethylsilane using conventional abbreviations for designation of major peaks: e.g. s, singlet; d, doublet; t, triplet; q, quartet; m, multiplet; br, broad.

Mass spectra (m/z) were recorded using a Fisons Instruments Trio mass spectrometer in the thermospray ionisation mode (TSP) or using a Finnigan navigator in electrospray ionisation mode (ES)—positive and/or negative ionisation mode.

As used herein, the term "column chromatography" refers to normal phase chromatography using silica gel (0.04–0.06 mm).

Room temperature includes 20 to 25° C.

PREPARATIVE EXAMPLES

Preparation 1

N-Propionylalanine

Trimethylsilyl chloride (52.4 ml, 0.41 mol) was added dropwise to an ice-cooled solution of D,L-alanine (16.71 g, 0.188 mol) and triethylamine (57.5 ml, 0.41 mol) in dichloromethane (190 ml). Once addition was complete, the solution was stirred at room temperature for 1 h, followed by 1 h at 40° C. The solution was then cooled to −10° C., propionyl chloride (16.29 ml, 0.188 mol) was added dropwise over 15 minutes and, once addition was complete, the reaction was stirred at −10° C. for 2 h, then 16 h at room temperature, before cooling in an ice-bath. Water (100 ml) was added, the mixture was stirred for 15 minutes, then the phases separated. The aqueous layer was evaporated under reduced pressure and the residue triturated with acetone. The resulting solid was filtered off, and the filtrate concentrated under reduced pressure, to give an oil. This oil was purified by column chromatography using DCM:MeOH:0.88 NH$_3$ $_{(aq)}$ (89:10:1) as eluant, to give the title compound (20 g; containing 33% triethylamine).

$^1$H NMR (DMSO d$_6$, 300 MHz): $\delta$=0.98 (t, 3H), 1.20 (d, 3H), 2.07 (q, 2H), 4.08 (m, 1H), 7.80 (d, 1H), 8.57–9.00 (br s, 1H)

Preparation 2

N-Methoxy-N-methyl-2-(propionylamino) propanamide 1-(3-Dimethylaminopropyl)-3-ethylcarbodiimide hydrochloride (16.2 g, 84.7 mmol) was added to a suspension of the title compound of Preparation 1 (14.85 g, 77.0 mmol), triethylamine (27.9 ml, 72.5 mmol), N,O-dimethyl hydroxylamine hydrochloride (7.5 g, 77 mmol) and 1-hydroxybenzotriazole hydrate (12.3 g, 80.85 mmol), in dichloromethane (450 ml) and the reaction stirred at room temperature for 23 h. The mixture was washed with water (250 ml) and sodium bicarbonate solution (120 ml), dried (MgSO$_4$), filtered and evaporated under reduced pressure. The residual oil was purified by column chromatography using DCM:MeOH (95:5) as eluant to afford the title compound (8.2 g).

$^1$H NMR (CDCl$_3$, 300 MHz): $\delta$=1.17 (t, 3H), 1.34 (d, 3H), 2.22 (q, 2H), 3.20 (s, 3H), 3.79 (s, 3H), 4.98 (m, 1H), 6.23 (br s, 1H)

Preparation 3

N-(3-Ethoxy-1-methyl-2-oxo-3-butenyl) propanamide tert-Butyl lithium (70 ml, 1.7M in pentane, 119 mmol) was added over 5 minutes to a cooled (−78° C.) solution of ethyl vinyl ether (11.4 ml, 119 mmol) in tetrahydrofuran (160 mL), and the solution allowed to warm to −5° C. over 1 h. The solution was then re-cooled to −60° C., and magnesium bromide diethyl etherate (30.73 g, 119 mmol) was added portionwise, so as to maintain an internal temperature of less than −50° C. The mixture was then allowed to warm to −5° C., stirred for 30 minutes, and re-cooled to −10° C. A solution of the title compound of Preparation 2 (2.8 g, 14.9 mmol) in THF (20 ml) was added dropwise, and the reaction then stirred at room temperature for 3 h. The mixture was poured into 10% aqueous citric acid solution (500 ml) and extracted with EtOAc (500 ml). The organic solution was dried (MgSO$_4$), filtered and evaporated under reduced pressure to give an oil. The crude product was purified by column chromatography using DCM as eluant to afford the title compound (1.8 g).

$^1$H NMR (CDCl$_3$, 300 MHz): $\delta$=1.18 (t, 3H), 1.38 (m, 6H), 2.23 (q, 2H), 3.83 (q, 2H), 4.54 (d, 1H), 5.24 (m, 2H), 6.35 (m, 1H)

Preparation 4

Ethyl 2-oxo-3-(propionylamino)butanoate Method A

Oxygen was bubbled through a cooled (−78° C.) solution of the title compound of Preparation 3 (1.0 g, 5.98 mmol) and pyridine (3.25 ml, 44.9 mmol) in DCM (85 ml) for 2 min. Ozone was then bubbled through for 5 min and the solution then purged with oxygen, and placed under a nitrogen atmosphere. Dimethylsulphide (3.25 ml, 44.9 mmol) was added dropwise over 5 minutes, the solution stirred for 1 h, and then allowed to warm to room temperature. The mixture was washed with water, dried (Na$_2$SO$_4$), filtered and evaporated under reduced pressure to give an oil. The crude product was purified by column chromatography using an elution gradient of DCM:Et$_2$O (100:0 to 50:50) to afford the title compound (395 mg).

Method B

4-Dimethylaminopyridine (122 mg, 1.0 mmol) was added to a solution of the title compound of preparation 1 (10.9 g, 75.0 mmol) in pyridine (18.2 ml, 225 mmol) and THF (75 ml). The solution was heated to reflux and then ethyl oxalyl chloride (16.8 ml, 150 mmol) was added dropwise over 1 h. For the first half of the addition, the reaction mixture stayed as a solution, however as more ethyl oxalyl chloride was added a white precipitate formed which did not redissolve. The mixture was heated for a further 3 h and then poured onto ice water (200 ml). The mixture was extracted with EtOAc (3×200 ml) and the combined organics were dried ($MgSO_4$), filtered and concentrated in vacuo to afford a pale brown oil. $NaHCO_3$ (3.58 g, 42.7 mmol) and EtOH (25 ml) were added and the mixture heated to reflux for 3.5 h. The reaction was cooled and filtered. The filtrate was concentrated to a pale brown oil. The crude product was purified by column chromatography (Pentane/EtOAc, 80:20 to 20:80) to afford the title compound as a yellow oil (3.95 g, 20.0 mmol, 26%).

$^1$H NMR ($CDCl_3$, 300 MHz): δ=1.18 (t, 3H), 1.38 (m, 6H), 2.23 (q, 2H), 4.38 (q, 2H), 5.18 (m, 1H), 6.02 (m, 1H)

Preparation 5

2-Butoxynicotinic Acid

2-Chloronicotinic acid (10.0 g, 63.5 mmol) was added to a solution of sodium (3 g, 130 mmol) in butanol (100 ml) at 80° C., and the resulting mixture heated under reflux for 4 hours. The reaction was allowed to cool, and partitioned between EtOAc and 2M HCl (to give pH 3–4), and the layers separated. The organic phase was washed with brine, concentrated under reduced pressure, redissolved in EtOAc, dried ($MgSO_4$), filtered and evaporated under reduced pressure, to give the desired product as a solid (11.9 g).

$^1$H NMR ($d_6$-DMSO, 400 MHz): δ=0.90 (t, 3H), 1.40 (m, 2H), 1.65 (m, 2H), 4.30 (t, 2H), 7.00 (m, 1H), 8.05 (d, 2H), 8.30 (d, 1H)

LRMS: m/z 196.3 ($MH^+$)

Preparation 6

2-Butoxy-5-iodonicotinic Acid

A mixture of the title compound of Preparation 5 (3.46 g, 17.7 mmol) and N-iodosuccinimide (6 g, 26.6 mmol) in trifluoroacetic acid:trifluoroacetic anhydride (4:1, 35 ml) was heated under reflux for 24 hours, with the exclusion of light. The cooled reaction mixture was concentrated under reduced pressure and the residue dissolved in EtOAc. This solution was then washed sequentially with water (twice), sodium thiosulphate solution (twice), 10% aqueous sodium citrate solution, 2N hydrochloric acid, and brine, then dried ($MgSO_4$), filtered and evaporated under reduced pressure. The crude product was triturated with pentane to afford the title compound as a white solid (3.86 g, 68%).

$^1$H NMR ($CDCl_3$, 300 MHz): δ=1.00 (t, 3H), 1.50 (m, 2H), 1.85 (m, 2H), 4.60 (t, 2H), 8.50 (s, 1H), 8.70 (s, 1H), 10.50 (br s, 1H)

LRMS: m/z 322 ($MH^+$)

Preparation 7

2-Butoxy-5-iodonicotinonitrile

N,N-Dimethylformamide (3 drops) was added to an ice-cold suspension of the title compound of Preparation 6 (2.25 g, 7.01 mmol) and oxalyl chloride (3.55 g, 28.0 mmol) in DCM (20 ml), and the reaction stirred at room temperature for 4 h. The mixture was concentrated under reduced pressure and the residue azeotroped with DCM. The acid chloride was resuspended in DCM (20 ml), cooled in an ice-bath, 0.88 ammonia (2 mL) was added and the solution stirred at room temperature for 30 min. The reaction mixture was diluted with DCM, washed with water, 2M HCl and brine, then dried ($MgSO_4$), filtered and evaporated under reduced pressure to give a brown solid. A solution of trifluoroacetic anhydride (1.82 g, 8.67 mmol) in dioxan (2 ml) was added to an ice-cold solution of the intermediate amide (1.85 g, 5.78 mmol) and pyridine (1.14 g, 14.4 mmol) in dioxan (15 ml), and the reaction stirred at room temperature for 3 h. The mixture was concentrated under reduced pressure and the residue partitioned between EtOAc and water, and the layers separated. The organic layer was washed with 2M HCl (twice), saturated sodium bicarbonate solution, and brine, then dried ($MgSO_4$), filtered and evaporated under reduced pressure. The crude product was purified by column chromatography using an elution gradient of pentane:EtOAc (100:0 to 95:5) to give the title compound.

$^1$H NMR ($CDCl_3$, 300 MHz): δ=0.98 (t, 3H), 1.50 (m, 2H), 1.80 (m, 2H), 4.40 (t, 2H), 8.08 (s, 1H), 8.50 (s, 1H)

LRMS: m/z 303.0 ($MH^+$)

Preparation 8

2-Butoxy-5-iodo-3-pyridinecarboximidamide Formate

The title compound of Preparation 7 (10 g, 33.1 mmol) was added to a freshly prepared solution of sodium (1.5 g, 65.2 mmol) in butanol (100 ml), and the reaction stirred at room temperature for 18 h. Ammonium formate (17.4 g, 276 mmol) was added and the reaction heated to 50° C. for 2 h, followed by a further 2 h at 80° C. The cooled mixture was concentrated under reduced pressure and the residue triturated with $Et_2O$. This solid was triturated with water, and then triturated several times with ether to afford the title compound (2.53 g), which was used without further purification.

$^1$H NMR ($d_6$-DMSO, 400 MHz): δ=0.90 (t, 3H), 1.39 (m, 2H), 1.69 (m, 2H), 4.30 (t, 2H), 8.28 (s, 1H), 8.42 (s, 1H), 8.59 (s, 1H)

Preparation 9

2-(2-Butoxy-5-iodo-3-pyridinyl)-7-ethyl-5-methylimidazo[5,1-f][1,2,4]triazin-4(3H)-one Method A Hydrazine monohydrate (194 μL, 3.98 mmol) was added to a solution of the title compound of Preparation 8 (2.02 g, 3.98 mmol) in ethanol (3.8 ml) and the solution stirred for 20 min. A solution of the title compound of Preparation 4 (800 mg, 3.98 mmol) in ethanol (1 ml) was added and the reaction heated at 70° C. for 2 h. The cooled mixture was concentrated under reduced pressure and the residue purified by column chromatography using DCM:$Et_2O$ (67:33) as eluant to give a yellow solid. This was triturated with ether to afford a yellow solid, 250 mg, (2:1 isomeric mixture of desired and undesired product). Phosphorous oxychloride (360 μL, 3.97 mmol) was added to a solution of this solid (243 mg, 0.516 mmol) in 1,2-dichloroethane (3 ml), and the reaction heated under reflux for 30 min. The cooled mixture was evaporated under reduced pressure and the residue partitioned between 2M sodium carbonate solution (5 ml) and EtOAc (5 ml), and the layers separated. The aqueous layer was extracted with EtOAc (2×5 ml) and the combined organic solutions dried ($MgSO_4$), filtered and evaporated under reduced pressure to give a yellow solid. The crude product was purified by column chromatography using DCM:Et$_2$O (91:9) as eluant to afford the title compound (130 mg).

Method B

Hydrazine monohydrate (91 μL, 1.87 mmol) was added to a suspension of the title compound of preparation 16 (834 mg, 1.87 mmol) in BuOH (8 ml) and the mixture was stirred at room temperature for 15 min. The title compound of preparation 4 (prepared by method B, 376 mg, 1.87 mmol) and NaHCO$_3$ (525 mg, 6.25 mmol) were added and the mixture was heated to reflux for 6 h. The mixture was then stirred at room temperature for 18 h and partitioned between water (100 ml) and DCM (2×150 ml). The combined organics were dried (Na$_2$SO$_4$), filtered and concentrated in vacuo to afford a brown oil. This was dissolved in DCM (15 ml), and POCl$_3$ (1.03 ml, 11.1 mmol) was added. The solution was heated to reflux for 1 h and then cooled to room temperature. Sat. NaHCO$_3$ soln. (100 ml) was added, and the mixture stirred for 1 h. The mixture was extracted with DCM (2×75 ml) and the combined organics were dried (Na$_2$SO$_4$), filtered and concentrated in vacuo to afford a brown solid. The crude product was purified by column chromatography (Pentane/EtOAc, 60:40) to afford the title compound as a beige solid (200 mg, 0.44 mmol, 24%).

$^1$H NMR (CDCl$_3$, 400 MHz): δ=1.01 (t, 3H), 1.41 (t, 3H), 1.58 (sextet, 2H), 1.88 (quintet, 2H), 2.63 (s, 3H), 3.05 (q, 2H), 4.56 (t, 2H), 8.50 (s, 1H), 8.76 (s, 1H), 9.80 (br s, 1H).

LRMS (ES+): m/z 454 (MH$^+$).

Combustion analysis: Calcd for C$_{17}$H$_{20}$IN$_5$O$_2$: C, 45.05; H, 4.45; N, 15.45. Found: C, 44.79; H, 4.27; N, 15.18.

Preparation 10

5-(2-Butoxy-5-trimethylsilylethynyl-3-pyridinyl)-2-[2-(dimethylamino)-ethyl]-3-ethyl-2,6-dihydro-7H-pyrazolo[4,3-d]pyrimidin-7-one Pd(PPh$_3$)$_2$Cl$_2$ (11.2 mg, 0.016 mmol), trimethylsilylacetylene (179 μl, 1.29 mmol) and cuprous iodide (3 mg, 0.016 mmol) were added to a stirred slurry of 5-(2-butoxy-5-iodo-3-pyridinyl)-2-[2-(dimethylamino)ethyl]-3-ethyl-2,6-dihydro-7H-pyrazolo[4,3-d]-pyrimidin-7-one (Example 44 in Annex 1, PCT Application, IB 00/01430) (330 mg, 0.647 mmol) in triethylamine (8 ml) and acetonitrile (2 ml) at room temperature under a nitrogen atmosphere. The mixture was heated at 60° C. for 3 h, cooled and extracted from brine with dichloromethane (2×100 ml). The organics were dried (MgSO$_4$), filtered and concentrated to give a yellow solid. Purification by flash column chromatography (elution with DCM/MeOH, 95:5) gave the title compound as a pale brown oil (290 mg, 93%).

$^1$H NMR (300 MHz, CDCl$_3$): δ=0.30 (s, 9H), 1.00 (t, 3H), 1.40 (t, 3H), 1.50 (m, 2H), 1.90 (m, 2H), 2.30 (s, 6H), 2.90 (t, 2H), 3.05 (q, 2H), 4.40 (t, 2H), 4.60 (t, 2H), 8.30 (s, 1H), 8.80 (s, 1H), 10.70 (s, 1H).

LRMS (TSP): m/z 481.3 (MH$^+$).

Preparation 11

5-(2-Butoxy-5-ethynyl-3-pyridinyl)-2-[2-(dimethylamino)ethyl]-3-ethyl-2,6-dihydro-7H-pyrazolo[4,3-d]pyrimidin-7-one Potassium fluoride (72.5 mg, 1.25 mmol) was added to a stirred solution of the title compound of preparation 10 (300 mg, 0.625 mmol) in N,N-dimethylformamide (10 ml) and water (2 ml) at room temperature. After 2 h the reaction mixture was poured into brine and extracted with EtOAc (2×100 ml) The organics were dried (MgSO$_4$), filtered and concentrated to give the product (285 mg) as a pale brown oil.

$^1$H NMR (300 MHz, CDCl$_3$): δ=1.00 (t, 3H), 1.40 (t, 3H), 1.50 (m, 2H), 1.90 (m, 2H), 2.30 (s, 6H), 2.90 (t, 2H), 3.00 (q, 2H), 4.40 (t, 2H), 4.60 (t, 2H), 8.40 (s,1H), 8.80 (s, 1H), 10.70 (s, 1H).

LRMS (ES+): m/z 409 (MH$^+$).

Preparation 12

5-(5-Acetyl-2-butoxy-3-pyridinyl)-2-[2-(dimethylamino)ethyl]-3-ethyl-2,6-dihydro-7H-pyrazolo[4,3-d]pyrimidin-7-one 1 N Sulfuric acid (1 ml) was added to a stirred solution of the title compound of preparation 11 (280 mg, 0.69 mmol) in acetone (8 ml) at room temperature. Mercury sulfate (40 mg, 0.14 mmol) was added and the mixture heated at reflux for 5 h. The reaction mixture was cooled, diluted with methanol (10 ml), filtered and the filtrate washed with further methanol. The solvent was evaporated and the residue partitioned between EtOAc (100 ml) and saturated sodium bicarbonate solution (100 ml). The aqueous was washed with a further 100 ml of EtOAc and the combined organics dried (MgSO$_4$), filtered and concentrated. Purification by flash column chromatography (elution with DCM/MeOH, 95:5) gave the product as a cream coloured solid (140 mg).

$^1$H NMR (300 MHz, CDCl$_3$): δ=1.00 (t, 3H), 1.40 (t, 3H), 1.50 (m, 2H), 1.90 (m, 2H), 2.30 (s, 6H), 2.60 (s, 3H), 2.90 (t, 2H), 3.05 (q, 2H), 4.40 (t, 2H), 4.70 (t, 2H), 8.80 (s, 1H), 9.20 (s, 1H), 10.60 (s, 1H).

LRMS (TSP): m/z 427.5 (MH$^+$).

Preparation 13

2-Ethoxy-5-iodonicotinamide

Oxalyl chloride (6.60 ml, 75.1 mmol) was added to a solution of 2-ethoxy-5-iodonicotinic acid (prepared according to the procedure in WO0127112, 20.0 g, 68.3 mmol) in DCM (400 ml) and N,N-dimethylformamide (0.1 ml) at 0° C. The solution was warmed to room temperature over 18 h and then concentrated in vacuo. The resultant orange oil was dissolved in THF (200 ml) and cooled to 0° C. NH$_3$ (410 ml of a 0.5 M soln. in dioxane, 205 mmol) was added and the mixture was warmed to room temperature over 4 h. The reaction mixture was concentrated in vacuo and triturated with water (150 ml). The solid was filtered and dried to afford the title compound as a beige solid (18.9 g, 64.9 mmol, 95%); m.p. 176–179° C.

$^1$H NMR (d$_6$-DMSO, 400 MHz): δ=1.35 (t, 3H), 4.40 (q, 2H), 7.60 (br s, 1H), 7.75 (br s, 1H), 8.30 (s, 1H), 8.50 (s, 1H).

LRMS (ES+): m/z 607 (2MNa$^+$).

Preparation 14

2-Butoxy-5-iodonicotinamide

A mixture of the title compound of preparation 13 (10.0 g, 34.0 mmol) and Cs$_2$CO$_3$ (5.60 g, 17.0 mmol) in BuOH (50 ml) was heated to reflux for 4.5 h and then stirred at room temperature for 18 h. The mixture was concentrated in vacuo and partitioned between water (200 ml) and DCM (2×250 ml). The combined organics were dried (Na$_2$SO$_4$), filtered and concentrated in vacuo. The crude product was triturated with Et$_2$O to afford the title compound as a beige solid (4.81 g, 15.0 mmol, 44%); m.p. 163–166° C.

$^1$H NMR (CDCl$_3$, 400 MHz): δ=1.00 (t, 3H), 1.50 (sextet, 2H), 1.80 (quintet, 2H), 4.50 (t, 2H), 6.00 (br s, 1H), 7.75 (br s, 1H), 8.45 (s, 1H), 8.75 (s, 1H).

LRMS (ES+): m/z 343 (MNa$^+$).

Combustion analysis: Calcd for C$_{10}$H$_{13}$IN$_2$O$_2$.0.15H$_2$O: C, 37.21; H, 4.15; N, 8.68. Found: C, 36.97; H, 3.92; N, 8.62.

Preparation 15

2-Butoxy-5-iodo-3-pyridinecarbothioamide

A mixture of the title compound of preparation 14 (4.81 g, 15.0 mmol) and Lawesson's reagent (3.04 g, 7.50 mmol) in toluene (40 ml) was heated at 90° C. for 2 h and then stirred at room temperature for a further 18 h. The reaction mixture was concentrated to half its volume and cooled to 0° C. The yellow precipitate was filtered and dried to afford the title compound (3.68 g, 10.9 mmol, 73%); m.p. 140–148° C.

$^1$H NMR (CDCl$_3$, 400 MHz): δ=1.00 (t, 3H), 1.45 (sextet, 2H), 1.80 (quintet, 2H), 4.50 (t, 2H), 8.00 (br s, 1H), 8.45 (s, 1H), 9.20 (br s, 1H), 9.25 (s, 1H).

LRMS (ES-): m/z 335 (M-H$^+$).

Preparation 16

Methyl 2-butoxy-5-iodo-3-pyridinecarbimidothioate Hydroiodide

The title compound of preparation 15 (3.68 g, 10.9 mmol) and iodomethane (1.5 ml, 24 mmol) were dissolved in DCM (20 ml) and acetone (30 ml) and stirred at room temperature for 3 days. The reaction mixture was concentrated in vacuo and triturated with Et$_2$O to afford the title compound as a brown solid (4.08 g, 8.53 mmol, 78%).

$^1$H NMR (d$_6$-DMSO, 400 MHz): δ=0.90 (t, 3H), 1.40 (sextet, 2H), 1.70 (quintet, 2H), 2.70 (s, 3H), 4.30 (t, 2H), 8.30 (s, 1H), 8.60 (s, 1H).

LRMS (ES+): m/z 351 (MH$^+$).

Preparation 17

2-(Propionylamino)-4-pentenoic Acid

Propionic anhydride (18.0 ml, 140 mmol) was added dropwise to a solution of DL-2-amino-4-pentenoic acid (14.6 g, 127 mmol) and K$_2$CO$_3$ (19.3 g, 140 mmol) in H$_2$O (100 ml) at 0° C. The reaction mixture was warmed to 20° C. and stirred for 18 h. Conc. HCl was added until the pH was 1, and the mixture was extracted with DCM (2×100 ml). The combined organics were dried (Na$_2$SO$_4$), filtered and concentrated in vacuo. The crude product was triturated with pentane (100 ml) to afford the title compound as white crystals (18.9 g, 110 mmol, 87%); mp 96–98° C.

$^1$H NMR (400 MHz, CDCl$_3$): δ=6.25 (d, 1H), 5.70 (m, 1H), 5.15 (d, 2H), 4.70 (q, 1H), 2.65 (m, 1H), 2.55 (m, 1H), 2.30 (q, 2H), 1.15 (t, 3H).

LRMS (ES+): m/z 172 (MH$^+$).

Combustion analysis: Calcd for C$_8$H$_{13}$NO$_3$: C, 56.13; H, 7.65; N, 8.18. Found: C, 56.04; H, 7.56; N, 8.11.

Preparation 18

N-Methoxy-N-methyl-2-(propionylamino)-4-pentenamide

2-Chloro-4,6-dimethoxy-1,3,5-triazine (14.47 g, 82.0 mmol) was added to a solution of the title compound of preparation 17 (12.74 g, 75.0 mmol) in THF (100 ml) and N-methylmorpholine (18.2 ml, 165 mmol) at 20° C. After 1 h a white precipitate had formed. N,O-dimethylhydroxylamine hydrochloride (7.80 g, 80.0 mmol) was added and the mixture was stirred at 20° C. for 3 days. The reaction mixture was concentrated in vacuo and partitioned between DCM (150 ml) and H$_2$O (50 ml). The aqueous phase was extracted with DCM (50 ml), and the combined organics were washed with 10% Na$_2$CO$_3$ soln. (50 ml) and 2M HCl (50 ml). The DCM solution was dried (Na$_2$SO$_4$), filtered and concentrated in vacuo. The crude product was purified by column chromatography (ethyl acetate) to afford the title compound as a yellow oil (12.3 g, 57.4 mmol, 77%).

$^1$H NMR (400 MHz, CDCl$_3$): δ=6.10 (br s, 1H), 5.70 (m, 1H), 5.10 (m, 3H), 3.8 (s, 3H), 3.20 (s, 3H), 2.55 (m, 1H), 2.40 (m, 1H), 2.20 (q, 2H), 1.15 (t, 3H).

LRMS (ES+): m/z 237 (MNa$^+$).

High resolution MS: m/z calcd for C$_{10}$H$_{18}$N$_2$O$_3$Na: 237.1210; found: 237.1213 (MNa$^+$).

Preparation 19

N-(1-Formyl-3-butenyl)propanamide

LiAlH$_4$ (1M in THF, 34.0 ml, 34.0 mmol) was added dropwise over 45 min to a solution of the title compound of preparation 18 (10.5 g, 49.0 mmol) in THF under N$_2$ at −10° C. The reaction was warmed to 20° C. and stirred for 3 h. KHSO$_4$ soln. (20 g in 150 ml H$_2$O) was cautiously added, and the mixture stirred for 10 min and then concentrated in vacuo to remove the THF. The aqueous phase was extracted with DCM (2×100 ml), and the combined organics were dried (Na$_2$SO$_4$), filtered and concentrated in vacuo. The crude product was purified by column chromatography (1:1, pentane/EtOAc) to afford the title compound as a yellow oil (3.30 g, 21.3 mmol, 43%).

$^1$H NMR (400 MHz, CDCl$_3$): δ=9.60 (s, 1H), 6.00 (br s, 1H), 5.70 (m, 1H), 5.10 (m, 2H), 4.60 (q, 1H2.60 (m, 2H), 2.20 (q, 2H), 1.15 (t, 3H).

Preparation 20

N-{1-[Cyano(hydroxy)methyl]-3-butenyl}propanamide

Acetone cyanohydrin (2.0 ml, 22 mmol) was added to a solution of the title compound of preparation 19 (3.30 g, 21.3 mmol) in DCM (50 ml) and Et$_3$N (3.1 ml) and the mixture was stirred for 18 h at 20° C. A further 0.5 ml of acetone cyanohydrin was added and the mixture stirred for a further 18 h. The reaction was concentrated in vacuo and the crude product purified by column chromatography (pentane/EtOAc, 60:40–40:60) to afford the title compound as a 1:1 mixture of diastereoisomers, yellow oil (2.35 g, 12.9 mmol, 61%).

$^1$H NMR (400 MHz, CDCl$_3$): δ=5.90 (m, 1H), 5.75 (m, 1H), 5.20 (m, 2H), 4.70 (m, 0.5H), 4.55 (m, 0.5H), 4.20 (m, 0.5H), 4.00 (m, 0.5H), 2.20–2.50 (m, 4H), 1.20 (m, 3H).

LRMS (ES+): m/z 205 (MNa$^+$).

High resolution MS: m/z calcd for C$_9$H$_{15}$N$_2$O$_2$: 183.1128; found: 183.1134 (MH$^+$).

Preparation 21

Ethyl 2-hydroxy-3-(propionylamino)-5-hexenoate

HCl was bubbled through a solution of the title compound of preparation 20 (2.35 g, 12.9 mmol) in EtOH (40 ml) at −10° C. until saturated. The reaction was warmed to 5° C. and the vessel was sealed and left in a refrigerator at 5° C. for 18 h. The reaction mixture was concentrated in vacuo, ice (−100 g) was added and the mixture warmed to 20° C. and stirred for 30 min. The aqueous phase was basified with 10% $Na_2CO_3$ soln. and extracted with DCM (100 ml). 2M HCl (50 ml) was added to the DCM extract and the mixture stirred for 30 min. The DCM layer was separated, washed with 10% $Na_2CO_3$ soln. (100 ml), dried ($Na_2SO_4$), filtered and concentrated in vacuo to an oil. All the aqueous phases were combined (pH ~6) and extracted with DCM (4×40 ml). The combined extracts were dried ($Na_2SO_4$), filtered and concentrated in vacuo to an oil. This was combined with the previous oil to afford the title compound (2.00 g, 8.7 mmol, 67%).

$^1$H NMR (400 MHz, $CDCl_3$): δ=5.60–5.80 (m, 2H), 5.10 (m, 2H), 4.40 (m, 1H) 4.20 (m, 3H), 3.40 (br s, 0.5H), 3.20 (br s, 0.5H), 2.40 (q, 1H), 2.20 (m, 3H), 1.30 (m, 3H), 1.10 (m, 3H).

LRMS (ES−): m/z 228 (M−H$^+$).

High resolution MS: m/z calcd for $C_{11}H_{20}NO_4$: 230.1387; found: 230.1395 (MH$^+$).

Preparation 22

Ethyl 2-oxo-3-(propionylamino)-5-hexenoate

Dess-Martin periodinane (4.25 g, 10 mmol) was added to a solution of the title compound of preparation 21 (2.00 g, 8.73 mmol) in DCM (40 ml) at 20° C. After 1.5 h, satd. $Na_2S_2O_3$ soln. (50 ml) and satd. $NaHCO_3$ soln. (50 ml) were added, and the mixture stirred for 30 min. The layers were separated, and the aqueous phase was extracted with DCM (2×50 ml). The combined organics were dried ($Na_2SO_4$), filtered and concentrated in vacuo. The crude product was purified by column chromatography (pentane/EtOAc, 75:25–25:75) to afford the title compound as a pale yellow oil (1.30 g, 5.72 mmol, 65%).

$^1$H NMR (400 MHz, $CDCl_3$): δ=6.00 (br s, 1H), 5.65 (tdd, 1H), 5.25 (q, 1H), 5.15 (dd, 1H), 5.10 (dd, 1H), 4.35 (q, 2H), 2.70 (dt, 1H), 2.50 (ddd, 1H), 2.25 (q, 2H), 1.35 (t, 3H), 1.15 (t, 3H).

LRMS (ES+): m/z 228 (MH$^+$), 250 (MNa$^+$).

High resolution MS: m/z calcd for $C_{11}H_{17}NO_4Na$: 250.1050; found: 250.1057 (MNa$^+$).

Preparation 23

5-Allyl-2-(2-butoxy-5-iodo-3-pyridinyl)-7-ethylimidazo[5,1-f][1,2,4]triazin-4(3H)-one Hydrazine monohydrate (0.11 ml, 2.25 mmol) was added to a suspension of the title compound of preparation 16 (1.00 g, 2.10 mmol) in BuOH (10 ml) and the mixture was tirred at room temperature for 15 min. The title compound of preparation 22 (470 mg, 2.07 mmol) and $NaHCO_3$ (600 mg, 7.06 mmol) were added and the mixture was heated to reflux for 6 h and then cooled to room temperature for 18 h. The mixture was partitioned between DCM (3×100 ml) and sat. $NaHCO_3$ soln. (50 ml), and the combined organics were dried ($Na_2SO_4$), filtered and concentrated in vacuo. The resultant brown oil was dissolved in 1,2-dichloroethane (10 ml) and to this was added $POCl_3$ (1.6 ml, 17.1 mmol). This solution was heated to reflux for 30 min and then cooled. 10% Aqueous $Na_2CO_3$ (20 ml) was added and the mixture stirred for 15 min. This mixture was partitioned between DCM (3×50 ml) and 10% aqueous $Na_2CO_3$ (50 ml), and the combined organics were were dried ($Na_2SO_4$), filtered and concentrated in vacuo. The resultant brown gum was purified by column chromatography (DCM/EtOAc, 80:20) and trituration with diisopropyl ether to afford the title compound as a beige solid (185 mg, 0.38 mmol, 18%); m.p. 134–135° C.

$^1$H NMR (400 MHz, $CDCl_3$): δ=9.90 (br s, 1H), 8.75 (s, 1H), 8.50 (s, 1H), 6.10 (ddt, 1H), 5.20 (dd, 1H), 5.10 (dd, 1H), 4.50 (t, 2H), 3.80 (d, 2H), 3.05 (q, 2H), 1.90 (pentet, 2H), 1.55 (sextet, 2H), 1.40 (t, 3H), 1.00 (t, 3H).

LRMS (ES+): m/z 480 (MH$^+$).

Combustion analysis: Calcd for $C_{19}H_{22}IN_5O_2$: C, 47.61; H, 4.63; N, 14.61. Found: C, 47.32; H, 4.56; N, 14.30.

Preparation 24

2-(2-Butoxy-5-iodo-3-pyridinyl)-7-ethyl-5-propylimidazo[5,1-f][1,2,4]triazin-4triazin-4(3H)-one The title compound of preparation 23 (75 mg, 0.156 mmol), tosyl hydrazide (120 mg, 0.645 mmol) and toluene (2 ml) were combined and heated to reflux for 5 h. The mixture was stirred at room temperature for 18 h and then partitioned between water (15 ml) and EtOAc (30 ml). The organic phase was washed with brine (10 ml) and 0.2M NaOH soln. (2×10 ml), dried ($Na_2SO_4$), filtered and concentrated to afford the title compound as a white solid (70 mg, 0.146 mmol, 93%).

$^1$H NMR (400 MHz, $CDCl_3$): δ=9.85 (br s, 1H), 8.75 (s, 1H), 8.50 (s, 1H), 4.5 (t, 2H), 3.05 (q, 2H), 3.00 (t, 2H), 1.90 (pentet, 2H), 1.80 (sextet, 2H), 1.55 (m, 2H), 1.40 (t, 3H), 1.00 (2 overlapping triplets, 6H).

LRMS (ES+): m/z 482 (MH$^+$).

Preparation 25

2-(2-Butoxy-5-iodo-3-pyridinyl)-7-ethyl-4-oxo-3,4-dihydroimidazo[5,1-f][1,2,4]triazine-5-carbaldehyde $NaIO_4$ (120 mg, 0.56 mmol) and $OsO_4$ (2.5% soln. In t-BuOH, 0.09 ml) were added to a solution of the title compound of preparation 23 (90 mg, 0.188 mmol) in THF (6 ml) and water (3 ml) and the mixture was stirred at room temperature for 18 h. The mixture was partitioned between EtOAc (50 ml) and water (30 ml), and the organic phase was dried ($Na_2SO_4$), filtered and concentrated in vacuo. The crude product was purified by column chromatography (pentane/EtOAc, 60:40 to 40:60) to afford the title compound as a pale yellow solid.

$^1$H NMR (400 MHz, $CDCl_3$): δ=10.55 (br s, 1H), 10.45 (s, 1H), 8.80 (s, 1H), 8.60 (s, 1H), 4.60 (t, 2H), 3.20 (q, 2H), 1.90 (pentet, 2H), 1.55 (m, 2H), 1.50 (t, 3H), 1.05 (t, 3H).

LRMS (ES−): m/z 466 (M−H$^+$).

High resolution MS: m/z calcd for $C_{17}H_{18}N_5IO_3$: 468.0527; found: 468.0518 (MH$^+$).

Preparation 26

2-(2-Butoxy-5-iodo-3-pyridinyl)-7-ethyl-5-(4-morpholinylmethyl)imidazo[5,1-f][1,2,4]triazin-4(3H)-one The title compound of preparation 25 (50 mg, 0.107 mmol), morpholine (0.015 ml, 0.172 mmol), AcOH (0.010 ml, 0.175 mmol) and $NaBH(OAc)_3$ (50 mg, 0.236 mmol) were combined in THF (2 ml) and stirred at room temperature for 3 days. The mixture was partitioned between DCM

Example 1

2-(5-Acetyl-2-butoxy-3-pyridinyl)-7-ethyl-5-methylimidazo[5, 1-f][1,2,4]triazin-4(3H)-one

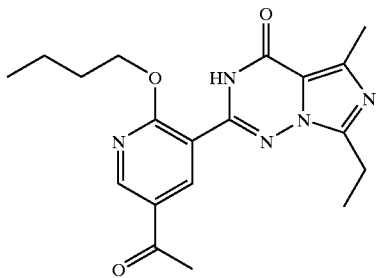

Butyl vinyl ether (1.30 ml, 10.0 mmol) and triethylamine (0.20 ml, 1.43 mmol) were added to a solution of the title compound of preparation 9 (prepared by method B, 200 mg, 0.44 mmol) in MeCN (5 ml). Pd(OAc)$_2$ (16 mg, 0.07 mmol) and tri-o-tolylphosphine (42 mg, 0.14 mmol) were added and the mixture was heated to reflux for 5 h and then stirred at room temperature for 18 h. The reaction was heated to reflux for a further 2 h, cooled and concentrated in vacuo. The resulting solid was suspended in 6M HCl (4 ml) and stirred for 1 h at room temperature. The reaction mixture was diluted with water (20 ml), and extracted with ethyl acetate (2×150 ml) and DCM (2×50 ml). The combined organics were dried (Na$_2$SO$_4$), filtered and concentrated in vacuo to yield a brown oil. The crude product was purified by column chromatography (DCM/MeOH, 98:2) to afford the title compound as a pale yellow solid, (40 mg, 0.11 mmol, 25%); m.p. 190–196° C.

$^1$H NMR (400 MHz, CDCl$_3$): δ=1.05 (t, 3H), 1.40 (t, 3H), 1.55 (sextet, 2H), 1.90 (quintet, 2H), 2.65 (2 superimposed singlets, 6H), 3.05 (q, 2H), 4.65 (t, 2H), 8.90 (s, 1H), 9.00 (s, 1H), 9.70 (br s, 1H).

LRMS (ES+): m/z 370 (MH$^+$).

Combustion analysis: Calcd for C$_{19}$H$_{23}$N$_5$O$_3$.0.2H$_2$O: C, 61.18; H, 6.32; N, 18.77. Found: C, 61.25; H, 6.23; N, 18.49.

Alternatively, example 1 may be prepared from the title compound of preparation 9 by following the procedure used to prepare the title compound of preparation 12 from example 44 in Annex 1, PCT Application, IB 00/01430.

(30 ml) and sat. NaHCO$_3$ soln. (20 ml). The organic phase was dried (Na$_2$SO$_4$), filtered and concentrated in vacuo to afford the title compound as a beige solid (38 mg, 0.071 mmol, 68%).

$^1$H NMR (400 MHz, CDCl$_3$): δ=8.75 (s, 1H), 8.50 (s, 1H), 4.50 (t, 2H), 4.00 (s, 2H), 3.75 (m, 4H), 3.10 (q, 2H), 2.65 (m, 4H), 1.85 (pentet, 2H), 1.50 (m, 2H), 1.40 (t, 3H), 1.00 (t, 3H).

LRMS (ES+): m/z 539 (MH$^+$).

High resolution MS: m/z calcd for C$_{21}$H$_{27}$N$_6$IO$_3$: 539.1262; found: 539.1260 (MH$^+$).

Example 2

2-(5-Acetyl-2-butoxy-3-pyridinyl)-7-ethyl-5-propylimidazo[5,1-f][1,2,4]triazin-4(3H)-one

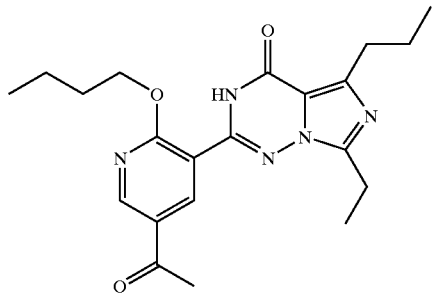

The title compound of preparation 24 (70 mg, 0.145 mmol), butyl vinyl ether (0.30 ml, 2.3 mmol), tri-o-tolylphosphine (10 mg, 0.06 mmol), triethylamine (0.05 ml, 0.36 mmol) and Pd(OAc)$_2$ (6 mg, 0.03 mmol) were combined in MeCN (2 ml), and the mixture was heated to reflux for 5 h and then cooled. 6M HCl (1 ml) was added and the mixture stirred for 15 min. Water (40 ml) was added and the solution extracted with EtOAc (50 ml). This was dried (Na$_2$SO$_4$), filtered and concentrated in vacuo. The crude product was purified by column chromatography (DCM/MeOH, 99.25:0.75 to 98.5:1.5) and trituration with diisopropylether to afford the title compound as a beige solid (14 mg, 0.035 mmol, 24%); m.p. 155–156° C.

$^1$H NMR (400 MHz, CDCl$_3$): δ=9.75 (br s, 1H), 9.00 (s, 1H), 8.90 (s, 1H), 4.65 (t, 2H), 3.10 (q, 2H), 3.00 (t, 2H), 2.65 (s, 3H), 1.90 (pentet, 2H), 1.80 (sextet, 2H), 1.55 (m, 2H), 1.40 (t, 3H), 1.00 (2 overlapping triplets, 6H).

LRMS (ES+): m/z 398 (MH$^+$).

High resolution MS: m/z calcd for C$_{21}$H$_{27}$N$_5$O$_3$: 398.2187; found: 398.2177 (MH$^+$).

Example 3

2-(5-Acetyl-2-butoxy-3-pyridinyl)-7-ethyl-5-(4-morpholinylmethyl)imidazo[5,1-f][1,2,4]triazin-4(3H)-one

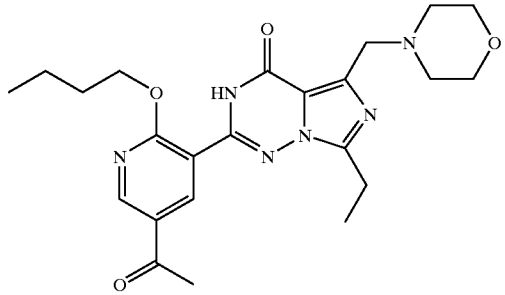

The title compound of preparation 26 (45 mg, 0.0835 mmol), butyl vinyl ether (0.18 ml, 1.38 mmol), tri-o-tolylphosphine (14 mg, 0.046 mmol), triethylamine (0.03 ml, 0.215 mmol) and Pd(OAc)$_2$ (5 mg, 0.0223 mmol) were combined in MeCN (1 ml), and the mixture was heated to reflux for 5 h and then cooled. The mixture was partitioned between DCM (30 ml) and sat. NaHCO$_3$ soln. (25 ml), and the aqueous phase was extracted further with DCM (2×20 ml). The combined organics were dried (Na$_2$SO$_4$), filtered and concentrated in vacuo. The crude product was purified by column chromatography (DCM/MeOH, 98:2 to 92:8) and trituration with diisopropylether to afford the title compound as a beige solid (15 mg, 0.033 mmol, 39%); m.p. 145–149° C.

$^1$H NMR (400 MHz, CDCl$_3$): δ=9.90 (br s, 1H), 9.10 (s, 1H), 8.90 (s, 1H), 4.70 (t, 2H), 4.00 (s, 2H), 3.75 (m, 4H), 3.10 (q, 2H), 2.65 (m, 4H), 2.65 (obscured singlet, 3H), 1.95 (pentet, 2H), 1.60 (m, 2H), 1.45 (t, 3H), 1.05 (t, 3H).

LRMS (ES+): m/z 455 (MH$^+$).

Biological Activity

Preferred compounds of formula (I) herein have in vitro activities as inhibitors of cGMP PDE5 with IC$_{50}$ values of less than about 10 nM. The compounds of examples 1 and 2 herein have cGMP PDE5 IC$_{50}$ (human corp. cav.) values of 1.34 nM and 1.96 nM respectively.

In vitro Metabolism Data

Table 1 illustrates the improved HLM half-life of the compound of example 1 versus a comparative example compound A.

| Example | HLM t$_{1/2}$ (min.) |
|---|---|
| 1 | 21 |
| Comound A | 4 |

Compound A is 2-[2-ethoxy-5-(4-ethyl-piperazin-1-yl-1-sulphonyl)-phenyl]-5-methyl-7-propyl-3H-imidazo[5,1-f][1,2,4]triazin-4-one also known as 1-[[3-(3,4-di hydro-5-methyl-4-oxo-7-propylimidazo[5, 1-f]-as-triazin-2-yl)-4-ethoxyphenyl]sulphonyl]-4-ethylpiperazine. Compound A can be prepared according to the methods detailed in examples 20, 19, 337 and 336 of published international application WO99/24433.

What is claimed is:

1. A compound of general formula I:

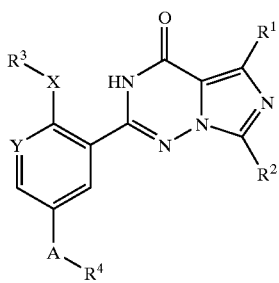

or pharmaceutically or veterinarily acceptable salt thereof wherein:

A represents CHOH or C=O;

X represents O or NR$^5$;

Y represents CH or N;

R$^1$ and R$^2$ independently represent H, C$_1$–C$_6$ alkyl, Het, C$_1$–C$_6$ alkylHet, aryl, C$_1$–C$_6$ alkylaryl, halo, cyano, nitro, OR$^6$, OC(O)R$^6$, C(O)R$^6$, C(O)OR$^6$, NR$^6$C(O)NR$^7$R$^8$, NR$^6$C(O)OR$^6$, OC(O)NR$^7$R$^8$, C(O)NR$^9$R$^{10}$, NR$^9$R$^{10}$, SO$_2$NR$^9$R$^{10}$ or SO$_2$R$^{11}$;

R$^3$, R$^4$ and R$^5$ independently represent H, C$_1$–C$_6$ alkyl, Het, C$_1$–C$_6$ alkylHet, aryl or C$_1$–C$_6$ alkylaryl;

or R$^3$ and R$^5$ together with the nitrogen atom to which they are bound can form a heterocyclic ring which is optionally substituted and/or terminated with one or more substituents selected from: halo, cyano, nitro, OR$^{12}$, OC(O)R$^{12}$, C(O)R$^{12}$, C(O)OR$^{12}$, NR$^{12}$C(O)NR$^{13}$R$^{14}$, NR$^{12}$C(O)OR$^{12}$, OC(O)NR$^{13}$R$^{14}$, C(O)NR$^{15}$R$^{16}$, NR$^{15}$R$^{16}$, SO$_2$NR$^{15}$R$^{16}$ or SO$_2$R$^{17}$;

wherein when R$^1$, R$^2$, R$^3$, R$^4$ or R$^5$ is a C$_1$–C$_6$ alkyl, Het, C$_1$–C$_6$ alkylHet, aryl or C$_1$–C$_6$ alkylaryl group, such C$_1$–C$_6$ alkyl, Het, C$_1$–C$_6$ alkylHet, aryl or C$_1$–C$_6$ alkylaryl group may be optionally substituted and/or terminated with one or more substituents selected from: halo, cyano, nitro, OR$^6$, OC(O)R$^6$, C(O)R$^6$, C(O)OR$^6$, NR$^6$C(O)NR$^7$R$^8$, NR$^6$C(O)OR$^6$, OC(O)NR$^7$R$^8$, C(O)NR$^9$R$^{10}$, NR$^9$R$^{10}$, SO$_2$NR$^9$R$^{10}$, SO$_2$R$^{11}$, C$_1$–C$_6$ alkyl, Het, C$_1$–C$_6$alkylHet, aryl or C$_1$–C$_6$ alkylaryl;

wherein when R$^1$, R$^2$, R$^3$, R$^4$ or R$^5$ is a C$_1$–C$_6$ alkyl, Het, C$_1$–C$_6$ alkylHet, aryl or C$_1$–C$_6$ alkylaryl group which is substituted and/or terminated with one or more substituents selected from: C$_1$–C$_6$ alkyl, Het, C$_1$–C$_6$ alkylHet, aryl or C$_1$–C$_6$ alkylaryl, such substituent groups are optionally substituted and/or terminated with one or more substituents selected from: halo, cyano, nitro, OR$^{12}$, OC(O)R$^{12}$, C(O)R$^{12}$, C(O)OR$^{12}$, NR$^{12}$C(O)NR$^{13}$R$^{14}$, NR$^{12}$C(O)OR$^{12}$, OC(O)NR$^{13}$R$^{14}$, C(O)NR$^{15}$R$^{16}$, NR$^{15}$R$^{16}$, SO$_2$NR$^{15}$R$^{16}$ or SO$_2$R$^{17}$;

R$^6$, R$^7$ and R$^8$ independently represent H, C$_1$–C$_6$ alkyl, Het, C$_1$–C$_6$ alkylHet, aryl or C$_1$–C$_6$ alkylaryl;

or R$^7$ and R$^8$ together with the nitrogen atom to which they are bound can form a heterocyclic ring which is optionally substituted and/or terminated with one or more substituents selected from: halo, cyano, nitro, OR$^{12}$, OC(O)R$^{12}$, C(O)R$^{12}$, C(O)OR$^{12}$, NR$^{12}$C(O)NR$^{13}$R$^{14}$, NR$^{12}$C(O)OR$^{12}$, OC(O)NR$^{13}$R$^{14}$, C(O)NR$^{15}$R$^{16}$, NR$^{15}$R$^{16}$, SO$_2$NR$^{15}$R$^{16}$ or SO$_2$R$^{17}$;

R$^9$ and R$^{10}$ independently represent H, C(O)R$^6$, SO$_2$R$^{11}$, C$_1$–C$_6$ alkyl, Het, C$_1$–C$_6$ alkylHet, aryl or C$_1$–C$_6$ alkylaryl;

or R$^9$ and R$^{10}$ together with the nitrogen atom to which they are bound can form a heterocyclic ring which is optionally substituted and/or terminated with one or more substituents selected from: halo, cyano, nitro, OR$^{12}$, OC(O)R$^{12}$, C(O)R$^{12}$, C(O)OR$^{12}$, NR$^{12}$C(O)NR$^{13}$R$^{14}$, NR$^{12}$C(O)OR$^{12}$, OC(O)NR$^{13}$R$^{14}$, C(O)NR$^{15}$R$^{16}$, NR$^{15}$R$^{16}$, SO$_2$NR$^{15}$R$^{16}$ or SO$_2$R$^{17}$;

R$^{11}$ represents C$_1$–C$_6$ alkyl, Het, C$_1$–C$_6$ alkylHet, aryl or C$_1$–C$_6$ alkylaryl;

wherein when R$^6$, R$^7$, R$^8$, R$^9$, R$^{10}$ or R$^{11}$ is a C$_1$–C$_6$ alkyl, Het, C$_1$–C$_6$ alkylHet, aryl or C$_1$–C$_6$ alkylaryl group, such C$_1$–C$_6$ alkyl, Het, C$_1$–C$_6$ alkylHet, aryl or C$_1$–C$_6$ alkylaryl group may be optionally substituted and/or terminated with one or more substituents selected from: halo, cyano, nitro, OR$^{12}$, OC(O)R$^{12}$, C(O)R$^{12}$, C(O)OR$^{12}$, NR$^{12}$C(O)NR$^{13}$R$^{14}$, NR$^{12}$C(O)OR$^{12}$, OC(O)NR$^{13}$R$^{14}$, C(O)NR$^{15}$R$^{16}$, NR$^{15}$R$^{16}$, SO$_2$NR$^{15}$R$^{16}$ or SO$_2$R$^{17}$;

R$^{12}$, R$^{13}$ and R$^{14}$ independently represent H or C$_1$–C$_6$ alkyl; or R$^{13}$ and R$^{14}$ together with the nitrogen atom to which they are bound can form a heterocyclic ring;

R$^{15}$ and R$^{16}$ independently represent H, C(O)R$^{12}$, SO$_2$R$^{17}$ or C$_1$–C$_6$ alkyl; or R$^{15}$ and R$^{16}$ together with the nitrogen atom to which they are bound can form a heterocyclic ring;

R$^{17}$ represents C$_1$–C$_6$ alkyl;

and wherein Het represents an optionally substituted four- to twelve-membered heterocyclic group, which group contains one or more heteroatoms selected from nitrogen, oxygen, sulfur and mixtures thereof;

with the proviso that when Y is CH and X is O and A is C(O) then $R^1$, $R^3$ and $R^4$ each do not represent $C_1$–$C_6$ alkyl and $R^2$ does not represent $C_1$–$C_6$ alkyl or $C_3$–$C_6$ cycloalkyl and with the further proviso that when Y is CH and X is O and A is CH(OH) then $R^1$ and $R^3$ each do not represent $C_1$–$C_6$ alkyl and $R^2$ does not represent $C_1$–$C_6$ alkyl or $C_3$–$C_6$ cycloalkyl and $R^4$ is not phenyl or $C_1$–$C_5$ alkyl optionally substituted with up to 2 substituents selected from hydroxy, phenyl, $NR^9R^{10}$ or $OC(O)R^6$ wherein $R^9$ and $R^{10}$ are H, $(C_1$–$C_6)$alkyl, $(C_1$–$C_6)$alkylphenyl or phenyl groups optionally substituted by hydroxy or $OR^{12}$ and $R^6$ is $(C_1$–$C_6)$alkyl optionally substituted by halogen or $OR^{12}$ and wherein $OR^{12}$ is $O(C_1$–$C_6)$alkyl.

2. Compound as defined in claim 1 wherein:

A represents CHOH or C=O;

X represents O;

Y represents CH or N;

$R^1$, $R^2$, $R^3$ and $R^4$ independently represent $C_1$–$C_6$ alkyl Het, $C_1$–$C_6$ alkylHet, aryl or $C_1$–$C_6$ alkylaryl optionally substituted and/or terminated with one or more substituents selected from: halo, $OR^6$, $NR^9R^{10}$, $C_1$–$C_6$ alkyl, Het, $C_1$–$C_6$ alkylHet, aryl or $C_1$–$C_6$ alkylaryl;

wherein when $R^1$, $R^2$, $R^3$ or $R^4$ is a $C_1$–$C_6$ alkyl, Het, $C_1$–$C_6$ alkylHet, aryl or $C_1$–$C_6$ alkylaryl group which is substituted and/or terminated with one or more substituents selected from: $C_1$–$C_6$ alkyl, Het, $C_1$–$C_6$ alkylHet, aryl or $C_1$–$C_6$ alkylaryl, such substituents are optionally substituted and/or terminated with one or more further substituents selected from: halo, $OR^{12}$ or $NR^{15}R^{16}$;

wherein $R^6$, $R^9$, $R^{10}$, $R^{12}$, $R^{15}$ and $R^{16}$ are as defined in claim 1 with the proviso that when Y is CH and X is O and A is C(O) then $R^1$, $R^3$ and $R^4$ each do not represent $C_1$–$C_6$ alkyl and $R^2$ does not represent $C_1$–$C_6$ alkyl or $C_3$–$C_6$ cycloalkyl and with the further proviso that when Y is CH and X is O and A is CH(OH) then $R^1$ and $R^3$ each do not represent $C_1$–$C_6$ alkyl and $R^2$ does not represent $C_1$–$C_6$ alkyl or $C_3$–$C_6$ cycloalkyl and $R^4$ is not phenyl or $C_1$–$C_5$ alkyl optionally substituted with up to 2 substituents selected from hydroxy, phenyl, $NR^9R^{10}$ or $OC(O)R^6$ wherein $R^9$ and $R^{10}$ are H, $(C_1$–$C_6)$alkyl, $(C_1$–$C_6)$alkylphenyl or phenyl groups optionally substituted by hydroxy or $OR^{12}$ and $R^6$ is $(C_1$–$C_6)$alkyl optionally substituted by halogen or $OR^{12}$ and wherein $OR^{12}$ is $O(C_1$–$C_6)$alkyl.

3. A compound as defined in claim 1:

wherein A represents CHOH or C=O;

X represents O;

Y represents N;

$R^1$, $R^2$, $R^3$ and $R^4$ independently represent $C_1$–$C_6$ alkyl, Het, $C_1$–$C_6$ alkylHet, aryl or $C_1$–$C_6$ alkylaryl optionally substituted and/or terminated with one or more substituents selected from: halo, $OR^6$, $NR^9R^{10}$, $C_1$–$C_6$ alkyl, Het, $C_1$–$C_6$ alkylHet, aryl or $C_1$–$C_6$ alkylaryl;

wherein when $R^1$, $R^2$, $R^3$ or $R^4$ is a $C_1$–$C_6$ alkyl, Het, $C_1$–$C_6$ alkylHet, aryl or $C_1$–$C_6$ alkylaryl group which is substituted and/or terminated with one or more substituents selected from: $C_1$–$C_6$ alkyl, Het, $C_1$–$C_6$ alkylHet, aryl or $C_1$–$C_6$ alkylaryl, such substituents are optionally substituted and/or terminated with one or more further substituents selected from: halo, $OR^{12}$ or $NR^{15}R^{16}$;

wherein $R^6$, $R^9$, $R^{10}$, $R^{12}$, $R^{15}$ and $R^{16}$ are as hereinbefore defined.

4. A compound according to claims 1 wherein A represents C=O.

5. A compound according to claim 1 of general formula (I) as defined hereinbefore wherein:

A represents C=O;

X represents O or $NR^5$;

Y represents CH or N;

$R^1$ and $R^2$ independently represent H, Het, $C_1$–$C_6$ alkylHet, aryl, $C_1$–$C_6$ alkylaryl, halo, cyano, nitro, $OR^6$, $OC(O)R^6$, $C(O)R^6$, $C(O)OR^6$, $NR^6C(O)NR^7R^8$, $NR^6C(O)OR^6$, $OC(O)NR^7R^8$, $C(O)NR^9R^{10}$, $NR^9R^{10}$, $SO_2NR^9R^{10}$ or $SO_2R^{11}$;

$R^3$ and $R^4$ independently represent H, Het, $C_1$–$C_6$ alkylHet, aryl or $C_1$–$C_6$ alkylaryl;

$R^5$ independently represents H, $C_1$–$C_6$ alkyl, Het, $C_1$–$C_6$ alkylHet, aryl or $C_1$–$C_6$ alkylaryl;

or $R^3$ and $R^5$ together with the nitrogen atom to which they are bound can form a heterocyclic ring which is optionally substituted and/or terminated with one or more substituents selected from: halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$ or $SO_2R^{17}$;

wherein when $R^1$, $R^2$, $R^3$ or $R^4$ is a $C_1$–$C_6$ alkyl, Het, $C_1$–$C_6$ alkylHet, aryl or $C_1$–$C_6$ alkylaryl group, such $C_1$–$C_6$ alkyl, Het, $C_1$–$C_6$ alkylHet, aryl or $C_1$–$C_6$ alkylaryl group may be optionally substituted and/or terminated with one or more substituents selected from: halo, cyano, nitro, $OR^6$, $OC(O)R^6$, $C(O)R^6$, $C(O)OR^6$, $NR^6C(O)NR^7R^8$, $NR^6C(O)OR^6$, $OC(O)NR^7R^8$, $C(O)NR^9R^{10}$, $NR^9R^{10}$, $SO_2NR^9R^{10}$, $SO_2R^{11}$, $C_1$–$C_6$ alkyl, Het, $C_1$–$C_6$ alkylHet, aryl or $C_1$–$C_6$ alkylaryl;

wherein when $R^1$, $R^2$, $R^3$ or $R^4$ is a Het, $C_1$–$C_6$ alkylHet, aryl or $C_1$–$C_6$ alkylaryl group which is substituted and/or terminated with one or more substituents selected from: $C_1$–$C_6$ alkyl, Het, $C_1$–$C_6$ alkylHet, aryl or $C_1$–$C_6$ alkylaryl, such substituent groups are optionally substituted and/or terminated with one or more substituents selected from: halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}C(O)NR^{15}R^{16}$, $NR^{15}R^{16}$, $SO_2NR^{15}R^{16}$ or $SO_2R^{17}$;

wherein when $R^4$ is a $C_1$–$C_6$ alkyl, Het, $C_1$–$C_6$ alkylHet, aryl or $C_1$–$C_6$ alkylaryl group, such $C_1$–$C_6$ alkyl, Het, $C_1$–$C_6$ alkylHet, aryl or $C_1$–$C_6$ alkylaryl group may be optionally substituted and/or terminated with one or more substituents selected from: halo, cyano, nitro, $OR^6$, $OC(O)R^6$, $C(O)R^6$, $C(O)OR^6$, $NR^6C(O)NR^7R^8$, $NR^6C(O)OR^6$, $OC(O)NR^7R^8$, $C(O)NR^9R^{10}$, $NR^9R^{10}$, $SO_2NR^9R^{10}$, $SO_2R^{11}$, $C_1$–$C_6$ alkyl, Het, $C_1$–$C_6$ alkylHet, aryl or $C_1$–$C_6$ alkylaryl;

wherein when $R^5$ is a $C_1$–$C_6$ alkyl, Het, $C_1$–$C_6$ alkylHet, aryl or $C_1$–$C_6$ alkylaryl group which is substituted and/or terminated with one or more substituents selected from: $C_1$–$C_6$ alkyl, Het, $C_1$–$C_6$ alkylHet, aryl or $C_1$–$C_6$ alkylaryl, such substituent groups are optionally substituted and/or terminated with one or more substituents selected from: halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$ or $SO_2R^{17}$;

$R^6$, $R^7$ and $R^8$ independently represent H, $C_1$–$C_6$ alkyl, Het, $C_1$–$C_6$ alkylHet, aryl or $C_1$–$C_6$ alkylaryl;

or $R^7$ and $R^8$ together with the nitrogen atom to which they are bound can form a heterocyclic ring which is optionally substituted and/or terminated with one or more substituents selected from: halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$ or $SO_2R^{17}$;

$R^9$ and $R^{10}$ independently represent H, $C(O)R^6$, $SO_2R^{11}$, $C_1-C_6$ alkyl, Het, $C_1-C_6$ alkylHet, aryl or $C_1-C_6$ alkylaryl;

or $R^9$ and $R^{10}$ together with the nitrogen atom to which they are bound can form a heterocyclic ring which is optionally substituted and/or terminated with one or more substituents selected from: halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$ or $SO_2R^{17}$;

$R^{11}$ represents $C_1-C_6$ alkyl, Het, $C_1-C_6$ alkylHet, aryl or $C_1-C_6$ alkylaryl;

wherein when $R^6$, $R^7$, $R^8$, $R^9$, $R^{10}$ or $R^{11}$ is a $C_1-C_6$ alkyl, Het, $C_1-C_6$ alkylHet, aryl or $C_1-C_6$ alkylaryl group, such $C_1-C_6$ alkyl, Het, $C_1-C_6$ alkylHet, aryl or $C_1-C_6$ alkylaryl group may be optionally substituted and/or terminated with one or more substituents selected from: halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$ or $SO_2R^{17}$;

$R^{12}$, $R^{13}$ and $R^{14}$ independently represent H or $C_1-C_6$ alkyl; or $R^{13}$ and $R^{14}$ together with the nitrogen atom to which they are bound can form a heterocyclic ring;

$R^{15}$ and $R^{16}$ independently represent H, $C(O)R^{12}$, $SO_2R^{17}$ or $C_1-C_6$ alkyl; or $R^{15}$ and $R^{16}$ together with the nitrogen atom to which they are bound can form a heterocyclic ring;

$R^{17}$ represents $C_1-C_6$ alkyl;

wherein Het represents an optionally substituted four- to twelve-membered heterocyclic group, which group contains one or more heteroatoms selected from nitrogen, oxygen, sulfur and mixtures thereof.

6. A compound according to claim 1 wherein Y is N and A is C(O) and $R^1$, $R^2$, $R^3$, $R^4$ and $R^5$ are independently selected from $C_1-C_4$ alkyl or $C_1-C_4$ alkylHet.

7. A compound according to claim 1 wherein Y is N and A is C(O) and $R^1$ is $C_1-C_4$ alkyl or $C_1-C_4$ alkylHet, $R^2$, $R^5$ and $R^4$ are independently $C_1-C_3$ alkyl and $R^3$ is $C_2-C_4$ alkyl.

8. A compound according to claim 1 wherein Het is selected from $C_5$ to $C_8$ membered ring systems containing at least one N and optionally O, S or mixtures thereof.

9. A compound selected from:

2-(5-Acetyl-2-butoxy-3-pyridinyl)-7-ethyl-5-methylimidazo[5,1-f][1,2,4]triazin-4(3H)-one;

2-(5-Acetyl-2-butoxy-3-pyridinyl)-7-ethyl-5-propylimidazo[5, 1-f][1,2,4]triazin-4(3H)-one;

2-(5-Acetyl-2-butoxy-3-pyridinyl)-7-ethyl-5-(4-morpholinylmethyl)imidazo[5,1-f][1,2,4]triazin-4(3H)-one; or 2-(5-Acetyl-2-butoxy-3-pyridinyl)-7-ethyl-5-(4-morpholinylethyl)imidazo[5,1-f][1,2,4]triazin-4(3H)-one or a pharmaceutically acceptable salt thereof.

10. A compound of formula (I):

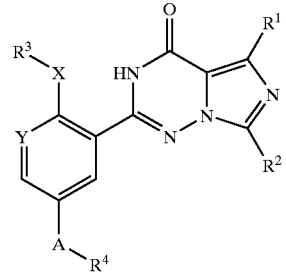

I or pharmaceutically or veterinarily acceptable salts, thereof wherein:

A represents CHOH or C=O;

X represents O or $NR^5$;

Y represents CH or N;

$R^1$ and $R^2$ independently represent H, $C_1-C_6$ alkyl, Het, $C_1-C_6$ alkylHet, aryl, $C_1-C_6$ alkylaryl, halo, cyano, nitro, $OR^6$, $OC(O)R^6$, $C(O)R^6$, $C(O)OR^6$, $NR^6C(O)NR^7R^8$, $NR^6C(O)OR^6$, $OC(O)NR^7R^8$, $C(O)NR^9R^{10}$, $NR^9R^{10}$, $SO_2NR^9R^{10}$ or $SO_2R^{11}$;

$R^3$, $R^4$ and $R^5$ independently represent H, $C_1-C_6$ alkyl, Het, $C_1-C_6$ alkylHet, aryl or $C_1-C_6$ alkylaryl;

or $R^3$ and $R^5$ together with the nitrogen atom to which they are bound can form a heterocyclic ring which is optionally substituted and/or terminated with one or more substituents selected from: halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$ or $SO_2R^{17}$;

wherein when $R^1$, $R^2$, $R^3$, $R^4$ or $R^5$ is a $C_1-C_6$ alkyl, Het, $C_1-C_6$ alkylHet, aryl or $C_1-C_6$ alkylaryl group, such $C_1-C_6$ alkyl, Het, $C_1-C_6$ alkylHet, aryl or $C_1-C_6$ alkylaryl group may be optionally substituted and/or terminated with one or more substituents selected from: halo, cyano, nitro, $OR^6$, $OC(O)R^6$, $C(O)R^6$, $C(O)OR^6$, $NR^6C(O)NR^7R^8$, $NR^6C(O)OR^6$, $OC(O)NR^7R^8$, $C(O)NR^9R^{10}$, $NR^9R^{10}$, $SO_2NR^9R^{10}$, $SO_2R^{11}$, $C_1-C_6$ alkyl, Het, $C_1-C_{16}$ alkylHet, aryl or $C_1-C_6$ alkylaryl;

wherein when $R^1$, $R^2$, $R^3$, $R^4$ or $R^5$ is a $C_1-C_6$ alkyl, Het, $C_1-C_6$ alkylHet, aryl and $C_1-C_6$ alkylaryl group which is substituted and/or terminated with one or more substituents selected from: $C_1-C_6$ alkyl, Het, $C_1-C_6$ alkylHet, aryl or $C_1-C_6$ alkylaryl, such substituent groups are optionally substituted and/or terminated with one or more substituents selected from: halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$ or $SO_2R^{17}$;

$R^6$, $R^7$ and $R^8$ independently represent H, $C_1-C_6$ alkyl, Het, $C_1-C_6$ alkylHet, aryl or $C_1-C_6$ alkylaryl;

or $R^7$ and $R^8$ together with the nitrogen atom to which they are bound can form a heterocyclic ring which is optionally substituted and/or terminated with one or more substituents selected from: halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$ or $SO_2R^{12}$;

$R^9$ and $R^{10}$ independently represent H, $C(O)R^6$, $SO_2R^{11}$, $C_1-C_6$ alkyl, Het, $C_1-C_6$ alkylHet, aryl or $C_1-C_6$ alkylaryl;

or $R^9$ and $R^{10}$ together with the nitrogen atom to which they are bound can form a heterocyclic ring which is optionally substituted and/or terminated with one or more substituents selected from: halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$ or $SO_2R^{17}$;

$R^{11}$ represents $C_1$–$C_6$ alkyl, Het, $C_1$–$C_6$ alkylHet, aryl or $C_1$–$C_6$ alkylaryl;

wherein when $R^6$, $R^7$, $R^8$, $R^9$, $R^{10}$ or $R^{11}$ is a $C_1$–$C_6$ alkyl, Het, $C_1$–$C_6$ aryl or $C_1$–$C_6$ alkylaryl group, such $C_1$–$C_6$ alkyl, Het, $C_1$–$C_6$ alkylHet, aryl or $C_1$–$C_6$ alkylaryl group may be optionally substituted and/or terminated with one or more substituents selected from: halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$ or $SO_2R^{17}$;

$R^{12}$, $R^{13}$ and $R^{14}$ independently represent H or $C_1$–$C_6$ alkyl; or $R^{13}$ and $R^{14}$ together with the nitrogen atom to which they are bound can form a heterocyclic ring;

$R^{15}$ and $R^{16}$ independently represent H, $C(O)R^{12}$, $SO_2R^{17}$ or $C_1$–$C_6$ alkyl, or $R^{15}$ and $R^{16}$ together with the nitrogen atom to which they are bound can form a heterocyclic ring;

$R^{17}$ represents $C_1$–$C_6$ alkyl;

Het represents an optionally substituted four- to twelve-membered heterocyclic group, which group contains one or more heteroatoms selected from nitrogen, oxygen, sulfur and mixtures thereof.

11. A formulation comprising a compound as defined in claim 1 in admixture with a pharmaceutically or veterinarily acceptable adjuvant, diluent or carrier.

12. A formulation as claimed in claim 11 which is a pharmaceutical formulation.

13. A formulation as claimed in claim 11, which is a veterinary formulation.

14. A method of treating male erectile dysfunction (MED), impotence, female sexual dysfunction (FSD), clitoral dysfunction, female hypoactive sexual desire disorder, female sexual arousal disorder, female sexual pain disorder or female sexual orgasimic dysfunction (FSOD) which comprises administering a therapeutically effective amount of a compound as claimed in claim 1 to a patient in need of such treatment.

* * * * *